US008926809B2

(12) United States Patent
Pletcher et al.

(10) Patent No.: US 8,926,809 B2
(45) Date of Patent: Jan. 6, 2015

(54) STANDBY BIASING OF ELECTROCHEMICAL SENSOR TO REDUCE SENSOR STABILIZATION TIME DURING MEASUREMENT

(71) Applicant: Google Inc., Mountain View, CA (US)

(72) Inventors: Nathan Pletcher, Mountain View, CA (US); Brian Otis, Sunnyvale, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/032,418

(22) Filed: Sep. 20, 2013

(65) Prior Publication Data

US 2014/0213867 A1 Jul. 31, 2014

Related U.S. Application Data

(63) Continuation of application No. 13/750,493, filed on Jan. 25, 2013.

(51) Int. Cl.
| | | |
|---|---|---|
| *A61B 5/1486* | (2006.01) | |
| *A61B 5/1495* | (2006.01) | |
| *A61B 5/00* | (2006.01) | |
| *A61B 5/145* | (2006.01) | |
| *A61B 5/1459* | (2006.01) | |

(52) U.S. Cl.
CPC ........... *A61B 5/0004* (2013.01); *A61B 5/14532* (2013.01); *A61B 5/1486* (2013.01); *A61B 5/1495* (2013.01); *A61B 5/6821* (2013.01); *A61B 5/7264* (2013.01); *A61B 5/742* (2013.01); *A61B 5/1459* (2013.01)
USPC .................. 204/403.14; 205/777.5; 600/245; 600/247; 600/356

(58) Field of Classification Search
CPC ... A61B 5/6821; A61B 5/1459; A61B 5/1486
USPC ..................... 351/159.03; 600/345, 347, 356; 204/403.01–403.14
See application file for complete search history.

(56) References Cited

U.S. PATENT DOCUMENTS

| | | |
|---|---|---|
| 3,958,560 A | 5/1976 | March |
| 4,014,321 A | 3/1977 | March |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Wang et al. (IEEE Electron Devices and Solid-State Circuits, Dec. 8-10, 2008).*

(Continued)

*Primary Examiner* — Luan Van
*Assistant Examiner* — Steven Rosenwald
(74) *Attorney, Agent, or Firm* — McDonnell Boehnen Hulbert & Berghoff LLP

(57) ABSTRACT

An eye-mountable device includes an electrochemical sensor embedded in a polymeric material configured for mounting to a surface of an eye. The electrochemical sensor applies a stabilization voltage between a working electrode and a reference electrode to allow the amperometric current to stabilize before powering measurement electronics configured to measure the amperometric current and communicate the measured amperometric current. The electrochemical sensor consumes less power while applying the stabilization voltage than during the measurement. The measurement is initiated in response to receiving a measurement signal at an antenna in the eye-mountable device.

17 Claims, 16 Drawing Sheets

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1* | 4/2002 | Moussy et al. ............... 600/345 |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,408 B1* | 7/2003 | Chan et al. ............... 204/403.15 |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,608,310 B2 | 12/2013 | Otis et al. |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0217173 A1 | 9/2008 | Varney et al. |
| 2008/0218696 A1 | 9/2008 | Mir |
| 2009/0030294 A1 | 1/2009 | Petisce et al. |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0036913 A1 | 2/2011 | Merz et al. |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |

(56) References Cited

U.S. PATENT DOCUMENTS

| | | |
|---|---|---|
| 2012/0041287 A1 | 2/2012 | Goodall et al. |
| 2012/0041552 A1 | 2/2012 | Chuck et al. |
| 2012/0067724 A1 | 3/2012 | Kahn et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 * | 9/2012 | Otis et al. ............... 600/345 |
| 2012/0259188 A1 | 10/2012 | Besling |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| JP | 2012-213640 | 11/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |
| WO | WO 2012/143370 A2 * | 10/2012 ............. G01N 27/00 |

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Bionic contact lens 'to project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-µW CMOS Glucose Sensor for Wireless Contact-Lens Tear Glucose Monitoring," IEEE Journal of Solid-State Circuits, Jan. 2012, pp. 335-344, vol. 47, No. 1.

Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

(56) References Cited

OTHER PUBLICATIONS

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh, et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

International Searching Authority, International Search Report and Written Opinion for International Application No. PCT/US2014/010666 mailed Apr. 18, 2014, 9 pages.

\* cited by examiner

STANDBY BIASING OF ELECTROCHEMICAL SENSOR TO REDUCE SENSOR STABILIZATION TIME DURING MEASUREMENT

CROSS REFERENCE TO RELATED APPLICATIONS

The present application is a continuation of U.S. patent application Ser. No. 13/750,493, filed Jan. 25, 2013, which is currently pending. The entire disclosure contents of this application are herewith incorporated by reference into the present application.

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode. A counter electrode and/or reference electrode is used to complete a circuit with the working electrode and allow the generated current to flow. When the working electrode is appropriately biased, the output current can be proportional to the reaction rate, so as to provide a measure of the concentration of the analyte surrounding the working electrode.

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

Some embodiments of the present disclosure provide a method including applying a stabilization voltage between a working electrode and a reference electrode in an eye-mountable device. The stabilization voltage can be sufficient to cause an analyte to undergo an electrochemical reaction at the working electrode. The method can include wirelessly receiving a measurement signal at an antenna in the eye-mountable device while the stabilization voltage is being applied. The method can include activating measurement electronics in the eye-mountable device to transition the measurement electronics from a standby mode to an active mode responsive to receiving the measurement signal. The measurement electronics can consume more power in the active mode than in the standby mode. The method can include, during the active mode, operating the measurement electronics to (i) measure an amperometric current through the working electrode, wherein the amperometric current is related to the analyte, and (ii) wirelessly communicate the measured amperometric current via the antenna.

Some embodiments of the present disclosure provide a method including wirelessly transmitting a stabilization signal by a reader during a stabilization period. The stabilization signal can be transmitted to an eye-mountable device comprising a working electrode, stabilization electronics, measurement electronics, and an antenna. The stabilization signal can be configured to cause the stabilization electronics to apply a stabilization voltage between the working electrode and the reference electrode. The stabilization voltage can be sufficient to cause an analyte to undergo an electrochemical reaction at the working electrode. The method can include a measurement signal by a reader during a measurement period following the stabilization period. The measurement signal can be transmitted to the eye-mountable device. The measurement signal can be configured to (i) cause the measurement electronics to measure an amperometric current through the working electrode, (ii) cause the measurement electronics to wirelessly communicate the measured amperometric current via the antenna, and (iii) supply power for powering the measurement electronics. The amperometric current can be related to the analyte. The method can include receiving an indication of the measured amperometric current by the reader. The indication of the measured amperometric current can be wirelessly communicated from the eye-mountable device.

Some embodiments of the present disclosure provide an eye-mountable device including a transparent polymeric material, an antenna, an electrochemical sensor, stabilization electronics, measurement electronics, and a controller. The transparent polymeric material can have a concave surface and a convex surface. The concave surface can be configured to be removably mounted over a corneal surface and the convex surface can be configured to be compatible with eyelid motion when the concave surface is so mounted. The electrochemical sensor can include a working electrode and a reference electrode. The stabilization electronics can be operable to apply a stabilization voltage between the working electrode and the reference electrode. The stabilization voltage can be sufficient to cause an analyte to undergo an electrochemical reaction at the working electrode. The measurement electronics can be configured, when activated, to (i) apply a measurement voltage between the working electrode and the reference electrode, (ii) measure an amperometric current through the working electrode, and (iii) use the antenna to communicate the measured amperometric current. The amperometric current can be related to the analyte. The controller can be configured to operate the stabilization electronics to apply the stabilization voltage during a stabilization period and to activate the measurement electronics during a measurement period in response to receiving a measurement signal via the antenna.

These as well as other aspects, advantages, and alternatives, will become apparent to those of ordinary skill in the art by reading the following detailed description, with reference where appropriate to the accompanying drawings.

DETAILED DESCRIPTION

Figure 1:
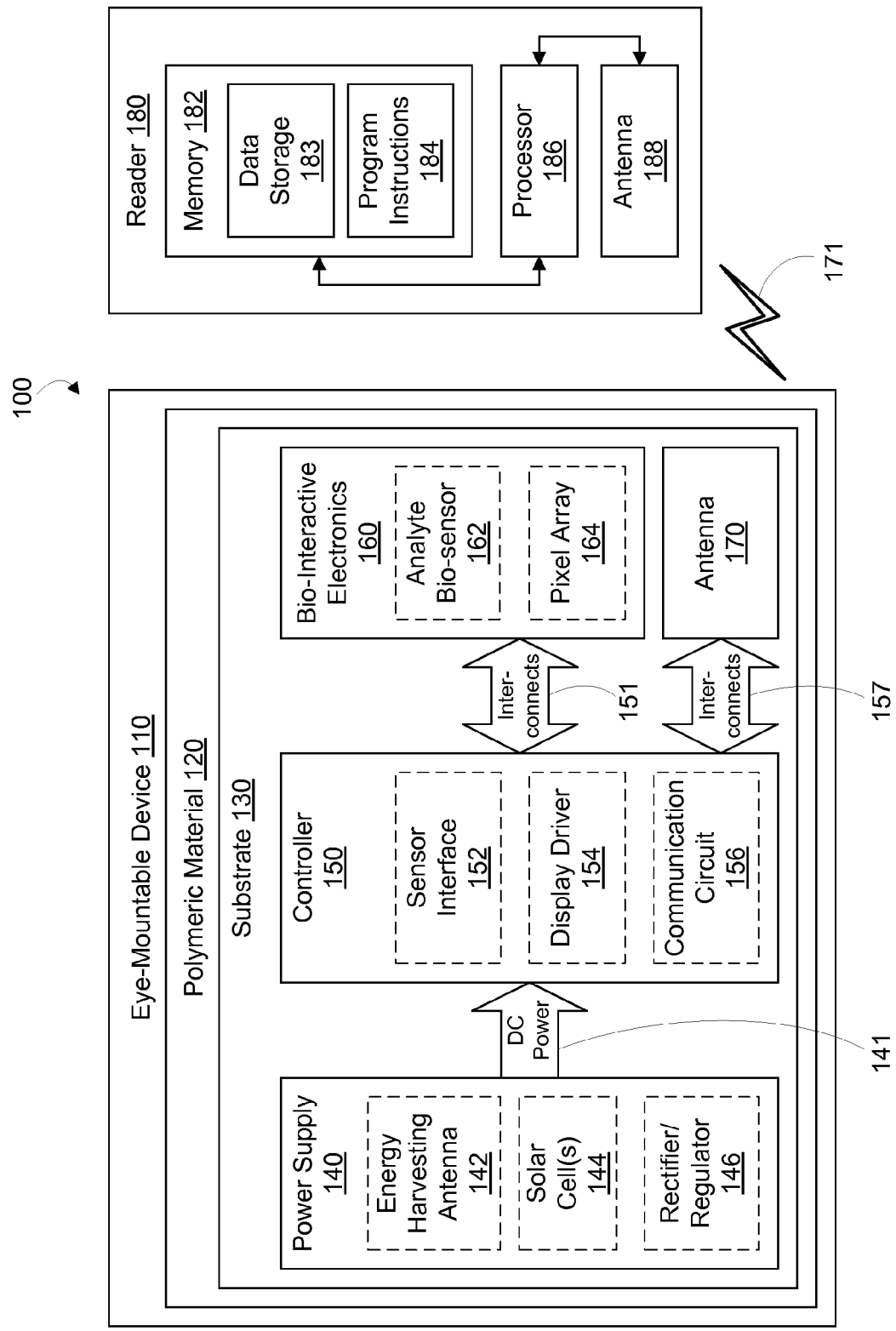
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An ophthalmic sensing platform or implantable sensing platform can include a sensor, control electronics and an antenna all situated on a substrate embedded in a polymeric material. The polymeric material can be incorporated in an ophthalmic device, such as an eye-mountable device or an implantable medical device. The control electronics can operate the sensor to perform readings and can operate the antenna to wirelessly communicate the readings from the sensor to an external reader via the antenna.

In some examples, the polymeric material can be in the form of a round lens with a concave curvature configured to mount to a corneal surface of an eye. The substrate can be embedded near the periphery of the polymeric material to avoid interference with incident light received closer to the central region of the cornea. The sensor can be arranged on the substrate to face inward, toward the corneal surface, so as to generate clinically relevant readings from near the surface of the cornea and/or from tear fluid interposed between the polymeric material and the corneal surface. Additionally or alternatively, the sensor can be arranged on the substrate to face outward, away from the corneal surface and toward the layer of tear fluid coating the surface of the polymeric material exposed to the atmosphere. In some examples, the sensor is entirely embedded within the polymeric material. For example, an electrochemical sensor that includes a working electrode and a reference electrode can be embedded in the polymeric material and situated such that the sensor electrodes are less than 10 micrometers from the polymeric surface configured to mount to the cornea. The sensor can generate an output signal indicative of a concentration of an analyte that diffuses through the lens material to the sensor electrodes.

The ophthalmic sensing platform can be powered via radiated energy harvested at the sensing platform. Power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the sensing platform from the harvested energy. The antenna can be arranged as a loop of conductive material with leads connected to the control electronics. In some embodiments, such a loop antenna can also wirelessly communicate the sensor readings to an external reader by modifying the impedance of the loop antenna so as to modify backscatter radiation from the antenna.

Tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. An ophthalmic sensing platform configured to measure one or more of these analytes can thus provide a convenient non-invasive platform useful in diagnosing and/or monitoring health states. For example, an ophthalmic sensing platform can be configured to sense glucose and can be used by diabetic individuals to measure/monitor their glucose levels.

In some embodiments of the present disclosure, when a voltage is first applied to electrodes in an electrochemical sensor, a large initial amperometric current may be generated due to build-up of analyte at the electrode during the time that no voltage is applied. Once the initial analyte build-up is consumed, the electrochemical reaction rate settles at a steady state value (e.g., where analyte diffusion compensates for electrochemical analyte consumption), at which point the reaction rate is approximately proportionate to the analyte concentration. Thus, when non-continuously (i.e., intermittently) sampling an analyte concentration, each reading may require a stabilization time to pass before the amperometric current settles at the steady state value.

Some embodiments of the present disclosure therefore provide systems and methods for intermittently sampling an electrochemical sensor by first applying voltage to electrochemical sensor electrodes to allow the current to stabilize, then reading the current. Such an intermittent measurement scheme reduces total power consumption, because measurement electronics are only powered while a measurement reading is being performed, and not during the initial stabilization period. During the stabilization period, a voltage is applied across the electrochemical sensor electrodes without also powering the measurement electronics. In some examples, a single power supply system can operate in both a high power setting (during the measurement) and a low setting (during the stabilization). In other examples, two separate power supplies can power the electrochemical sensor in a high power setting and low power setting, respectively. For example, a first power supply can apply voltage between the sensor electrodes during the stabilization period preceding a measurement. A second power supply, alone or in combination with the first power supply, can then power the measurement electronics during a measurement event to both sense the stabilized amperometric current and communicate the results.

The techniques described herein for intermittently measuring a pre-stabilized amperometric current from pre-charged sensor electrodes reduces total power consumption in an electrochemical sensor, relative to a system that powers measurement electronics while the sensor current reaches a stable value. The technique can be employed in applications with strict power budgets, such as in implantable medical devices or in electrochemical sensors included in an eye-mountable device.

The sensing platform can be powered by an energy harvesting system to capture energy from incident radiation, rather than by internal energy storage devices requiring more space. For example, power can be provided by light energizing photovoltaic cells included on the sensing platform. Power may also be provided by radio frequency (RF) energy harvested via a loop antenna. A rectifier and/or regulator can be incorporated with the control electronics to generate a stable DC voltage to power the sensing platform from the harvested RF energy. Furthermore, the control electronics can wirelessly communicate the sensor readings to an external reader by modifying the impedance of the loop antenna so as to characteristically modify the backscatter from the antenna.

In addition to the DC voltage for powering the control electronics (i.e., the measurement and communication circuitry), the energy harvesting system can also generate a voltage to apply to the sensor electrodes of the electrochemical sensor without also powering the measurement electronics. The voltage applied to the sensor electrodes may be referred to as a stabilization voltage and may be used to pre-charge the sensor electrodes prior to performing an amperometric current measurement. The eventual amperometric current measurement thereby avoids the transient effects in the amperometric current described above that occur immediately after applying voltage across the sensor electrodes.

The energy harvesting system can therefore operate in a standby mode in which the stabilization voltage is applied across sensor electrodes without also powering the control electronics. The system can also operate in a measurement mode in which a DC voltage is supplied to the control electronics to cause the sensing platform to perform a current measurement and communicate the result. During the high power mode, the voltage across the sensor electrodes can be maintained through the control electronics, such as by a potentiostat that simultaneously applies a voltage across the electrodes and measures the resulting amperometric current through the working electrode. Moreover, the energy harvesting system may include multiple energy harvesting devices, with one dedicated to providing a stabilization voltage and another dedicated to powering the sensing platform for measurement and communication. For example, an antenna may be used to harvest energy from incident radio frequency radiation and a photovoltaic cell may be used to harvest energy from incident light. In one example, the photovoltaic cell may be used to provide the stabilization voltage during the low power mode, and the antenna may be used to power the control electronics (e.g., a potentiostat and a backscatter communication circuit) during the high power mode.

An external reader can radiate radio frequency radiation to power the sensor via the energy harvesting system. The external reader may thereby control the operation of the sensing platform by controlling the supply of power to the sensing platform. In some examples, the external reader can operate to intermittently interrogate the sensing platform to provide a reading by radiating sufficient radiation to power the sensing platform to obtain a measurement and communicate the result. The external reader can also store the sensor results communicated by the sensing platform. In this way, the external reader can acquire a series of analyte concentration measurements over time without continuously powering the sensing platform.

In some embodiments of the present disclosure, the external reader is configured to cause the sensing platform to operate according to the sensor electrode pre-charge technique described herein. For example, the external reader can first send a stabilization signal to the sensing platform to initiate a low power stabilization mode, then send a measurement signal to the sensing platform to initiate a measurement. Following the measurement, the external reader may cease radiating entirely, and the sensing platform can enter an idle mode until the external reader sends the next stabilization signal to pre-charge the sensor.

In examples where the sensing platform enters the stabilization mode and the measurement mode in response to control signals from the external reader, the duration of the stabilization mode may be controlled by the external reader. That is, the period during which the sensor electrodes are pre-charged prior to obtaining a measurement can be controlled by the external reader by adjusting the time between the initiation of the stabilization mode and the initiation of the measurement mode. The reader can thus set the stabilization period to allow sufficient time for the amperometric current to reach a steady value and may be determined based on the duty cycle of the system, the duration of an idle period between subsequent measurement modes, and/or empirically determined factors.

In some examples, the sensing platform can communicate two sensor readings to allow the reader to determine whether the amperometric current is at a steady value. For example, if the two sensor readings are approximately equal, the reader may determine that the measured current is at its steady value, and therefore the reading can be used to estimate the analyte concentration level. The reader may also conclude that the duration of the stabilization time preceding such a steady-state reading was sufficient to allow the current to reach a stable value and may therefore employ a similar duration under similar circumstances. On the other hand, if the two sensor readings are not approximately equal, the reader may determine that the measured current is still undergoing transient variations and has not yet reached a steady state level. In such a case, the reader may conclude that the duration of the stabilization time was insufficient to allow the current to reach a stable value.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOD") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

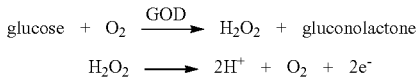

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or a group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
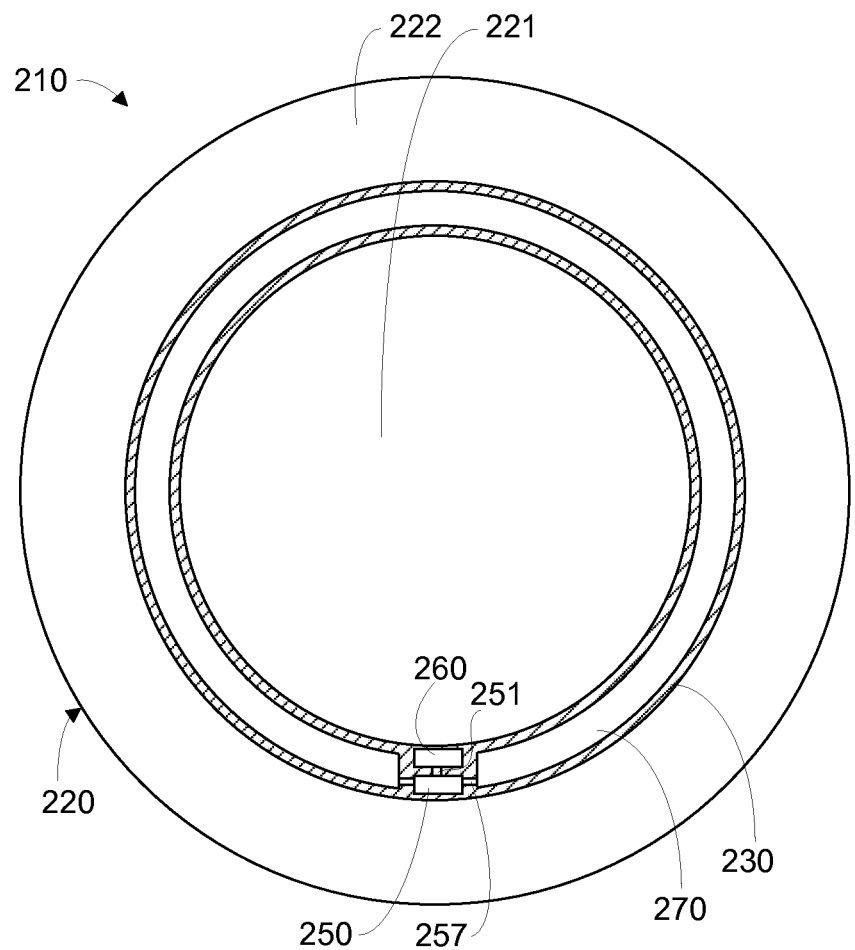
FIG. 2A is a bottom view of an example eye-mountable device.
Figure 2B:
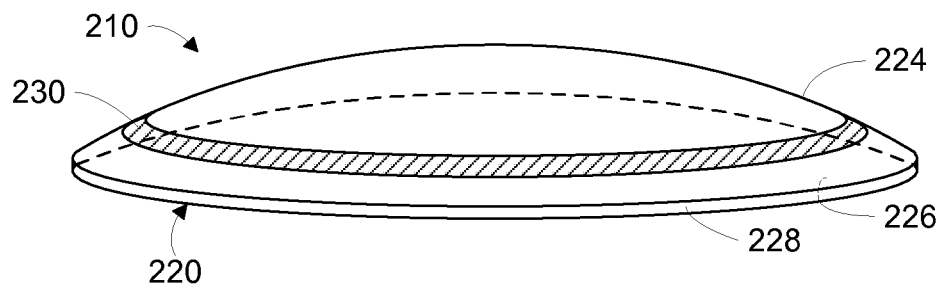
FIG. 2B is a side view of the example eye-mountable device shown in FIG. 2A.

FIG. 2A is a bottom view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes an analyte bio-sensor, for example, mounting such a bio-sensor on the substrate 230 to be close to the concave surface 226 allows the bio-sensor to sense analyte concentrations in tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
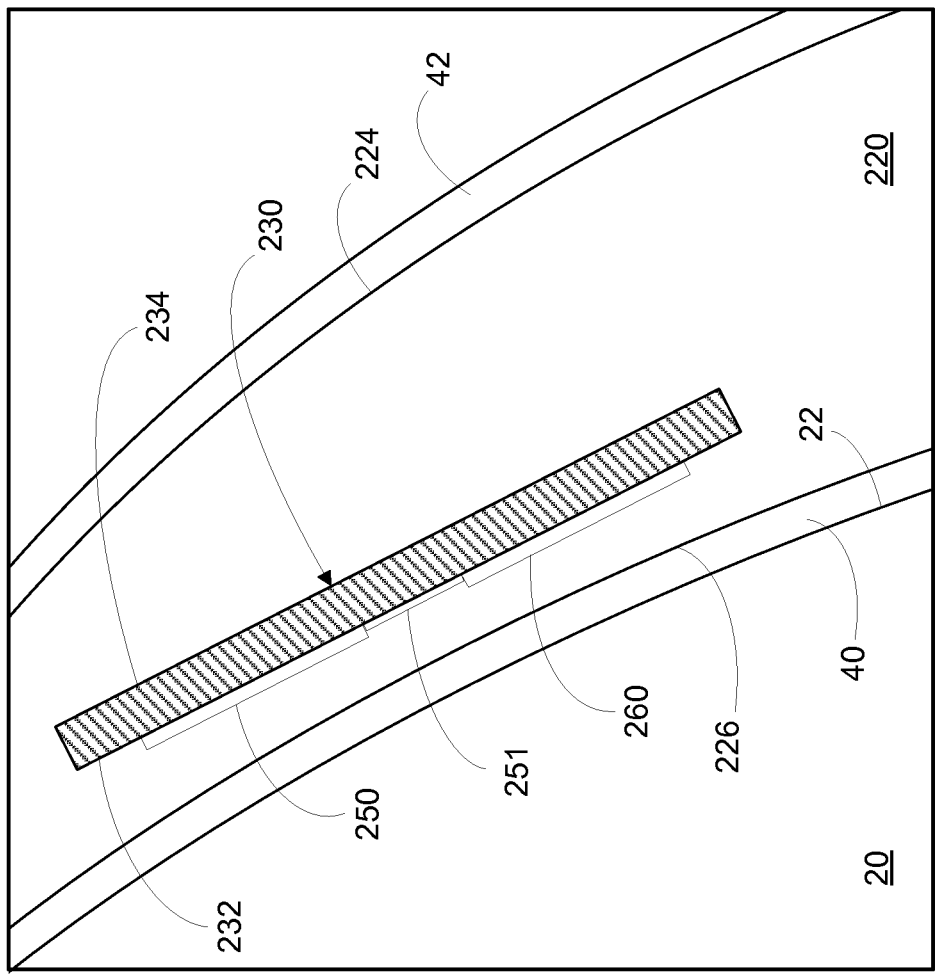
FIG. 2D is a side cross-section view enhanced to show the tear film layers surrounding the surfaces of the example eye-mountable device when mounted as shown in FIG. 2C.
Figure 2C:
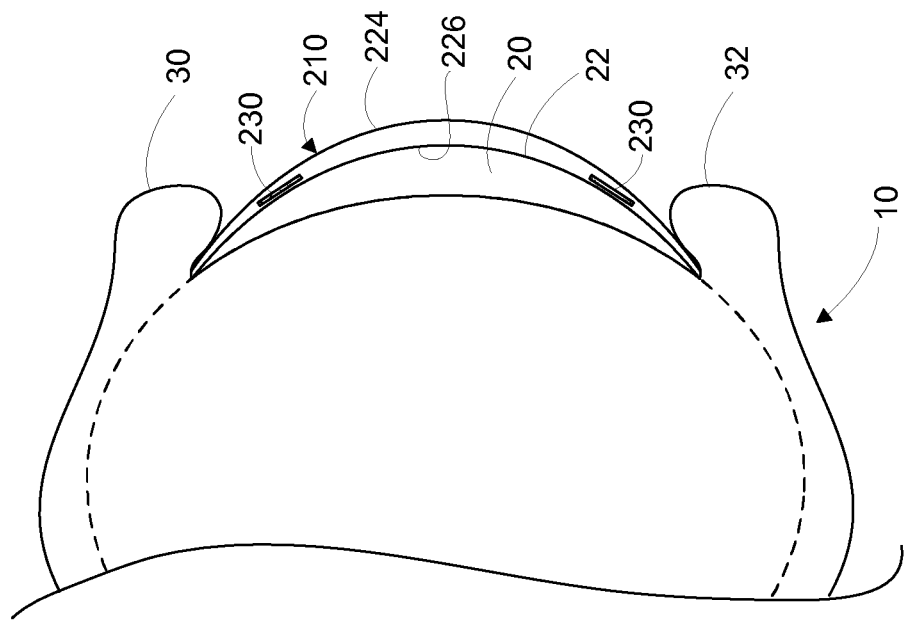
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the inward-facing surface 232 such that the bio-interactive electronics 260 are relatively closer in proximity to the corneal surface 22 than if they were mounted on the outward-facing surface 234.

III. An Ophthalmic Electrochemical Analyte Sensor

Figure 3:
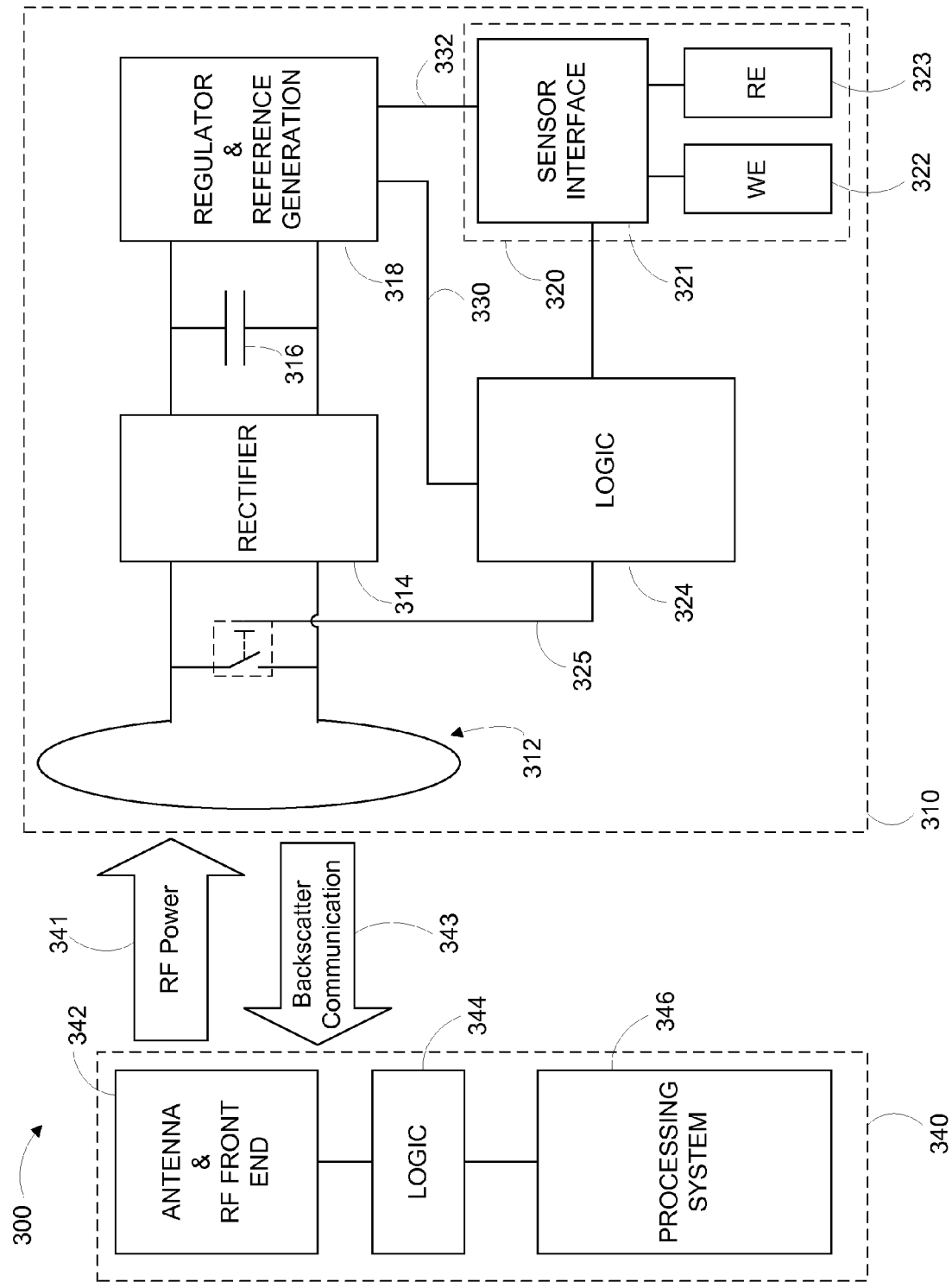
FIG. 3 is a functional block diagram of an example system for electrochemically measuring a tear film analyte concentration.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating the impedance of the antenna 312. An impedance modulator 325 (shown symbolically as a switch in FIG. 3) can be used to modulate the antenna impedance according to instructions from the hardware logic 324. Similar to the eye-mountable devices 110, 210 discussed above in connection with FIGS. 1 and 2, the eye-mountable device 310 can include a mounting substrate embedded within a polymeric material configured to be mounted to an eye.

The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22). In some embodiments, however, an electrochemical sensor can be situated on a mounting surface of such a substrate distal the surface of the eye (e.g., corresponding to the outward-facing side 234 of the substrate 230) to measure analyte concentration in a tear film layer coating the exposed surface of the eye-mountable device 310 (e.g., the outer tear film layer 42 interposed between the convex surface 224 of the polymeric material 210 and the atmosphere and/or closed eyelids).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory through a network).

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
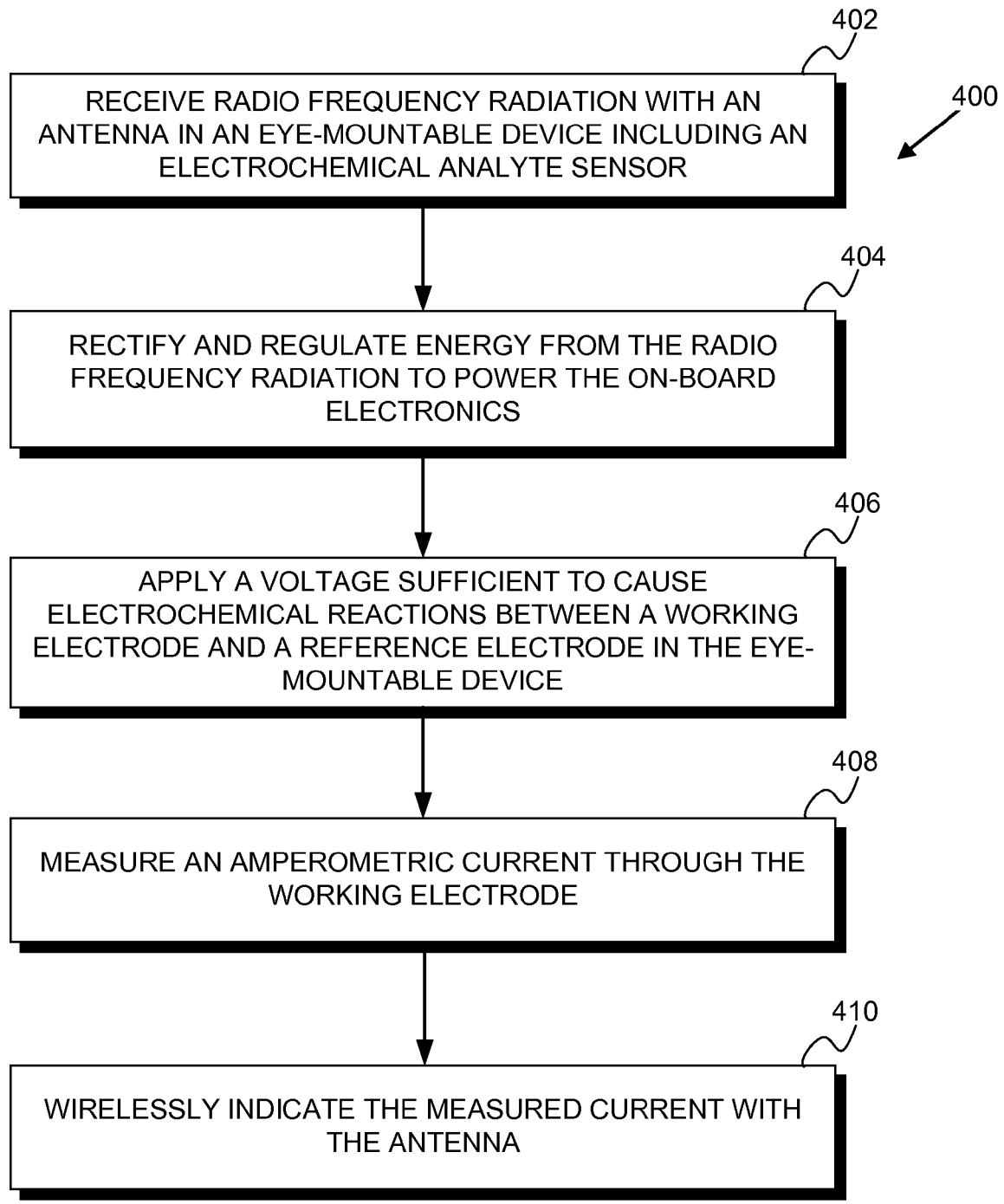
FIG. 4A is a flowchart of an example process for operating an amperometric sensor in an eye-mountable device to measure a tear film analyte concentration.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
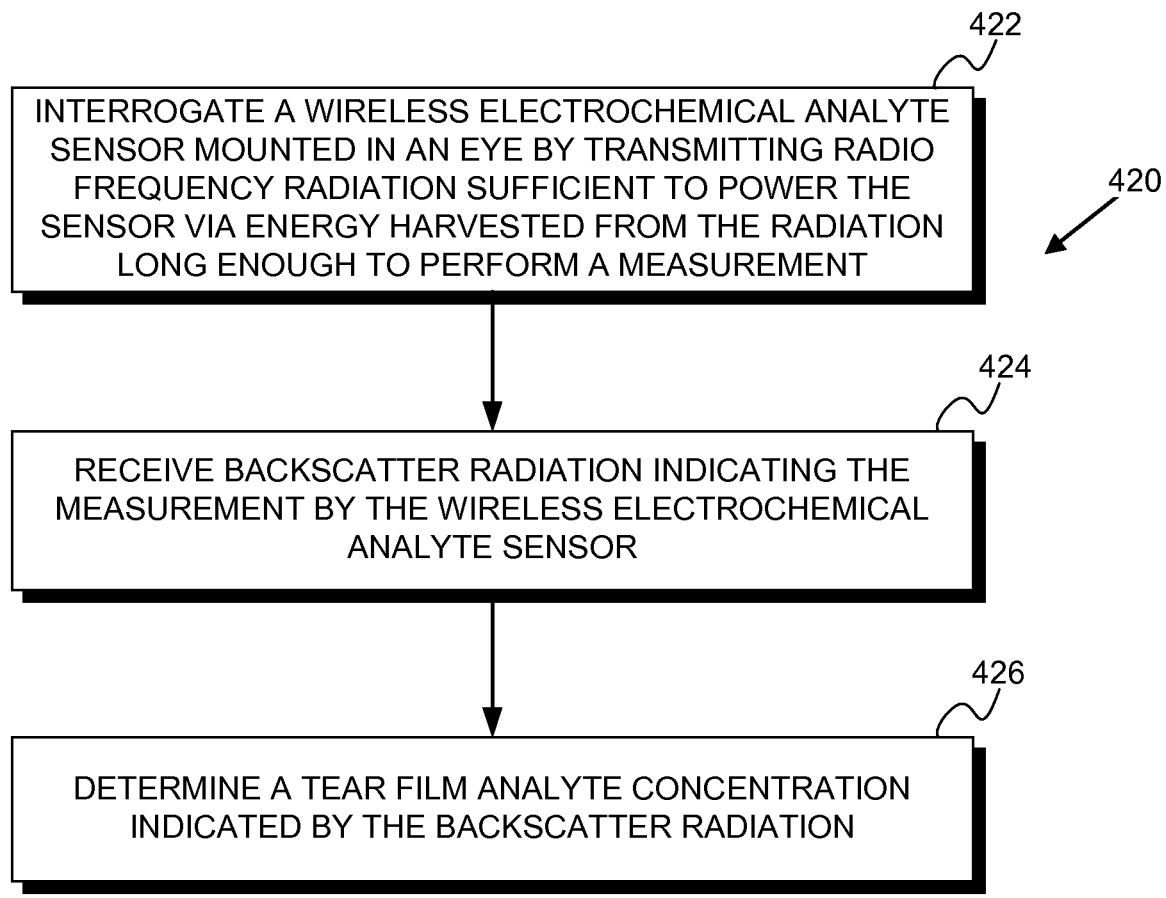
FIG. 4B is a flowchart of an example process for operating an external reader to interrogate an amperometric sensor in an eye-mountable device to measure a tear film analyte concentration.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

IV. Example Electrochemical Sensor

Figure 5A:
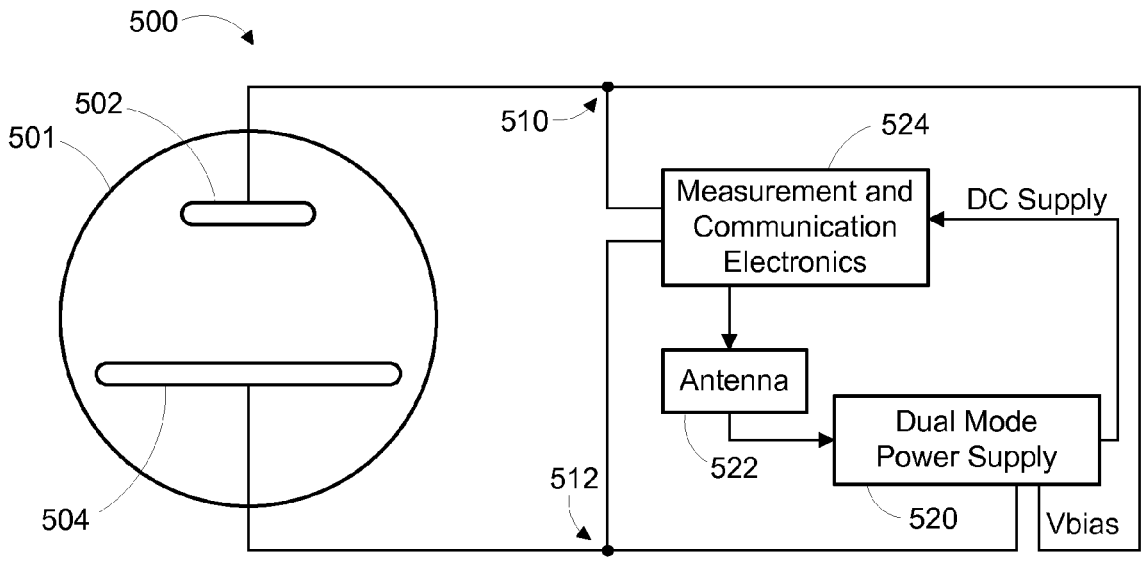
FIG. 5A is a functional block diagram of an example electrochemical sensor system including a dual mode power supply.

FIG. 5A is a functional block diagram of an example electrochemical sensor system 500 including a dual mode power supply 520. The electrochemical sensor system 500 can also include a working electrode 502, a reference electrode 504, an antenna 522, and measurement and communication electronics 524. The dual mode power supply 520 is electrically connected to the measurement and control electronics 524 to supply power (e.g., a DC supply voltage). For expediency, the measurement and control electronics 524 is alternately referred to herein as the "measurement electronics" or the "measurement module." The dual mode power supply 520 is also electrically connected to the sensor electrodes 502, 504 to apply a bias voltage (e.g., Vbias) across the sensor electrodes 502, 504. Thus, the working electrode 502 may be connected to both the measurement and communication electronics 524 and the dual mode power supply 520 at a node 510. Similarly, the reference electrode 504 may be connected to both the measurement and communication electronics 524 and the dual mode power supply at a node 512. Although, it is noted that functional block diagram of the system 500 shown in FIG. 5A illustrates separate functional modules, which are not necessarily implemented as physically distinct modules. For example, the dual mode power supply 520 and measurement and communication electronics 524 can be packaged in a common chip that includes terminals connected to the antenna 522 and the sensor electrodes 502, 504. Further, while not specifically illustrated, it is noted that a reagent layer can be provided on or near the working electrode 502 to sensitize the electrochemical sensor to an analyte of interest. For example, glucose oxidase may be fixed around the working electrode 502 (e.g., by incorporating glucose oxidase in a gel or medium) to cause the electrochemical sensor system 500 to detect glucose.

The dual mode power supply 520 is configured to provide power to the electrochemical sensor system 500 both in a standby mode and an active measurement mode. For example, during an active measurement mode, the dual mode power supply 520 can provide a DC supply voltage to the measurement and communication electronics 524 to thereby activate the measurement and control electronics 524. The DC supply voltage can be, for example, a DC voltage sufficient to turn on the measurement and control electronics 524. The measurement and control electronics 524 can be configured to measure an amperometric current through the working electrode 502 and use the antenna 522 to communicate the measured amperometric current. Thus, providing the DC supply voltage from the dual mode power supply 520 causes the system 500 to operate to obtain a measurement and wirelessly communicate the result.

The dual mode power supply 520 can be configured to provide power to the electrochemical sensor system 500 both in a standby mode and an active measurement mode. For example, in the standby mode, a bias voltage can be applied across the sensor electrodes 502, 504 to generate an amperometric current. However, while in the standby mode, the measurement and communication electronics 524 can be unpowered (e.g., no DC supply voltage conveyed from the dual mode power supply 520) in order to consume a relatively low level of power during the standby mode. In the active measurement mode, the measurement and communication electronics 524 can be turned on by providing an adequate DC supply voltage from the dual mode power supply 520.

In some embodiments, the dual mode power supply 520 can be similar to the voltage regulator and/or rectifier 314, 318 described in connection with FIG. 3 that outputs both an analog voltage 332 to the sensor interface 321, and a DC supply voltage 330 to the circuit logic 324. With reference to the system 500 in FIG. 5, the bias voltage (e.g., Vbias) applied across the sensor electrodes 502, 504 may be analogous to the analog voltage output of the energy harvesting system, while the DC supply voltage provided to the measurement and communication electronics 524 can be analogous to the digital voltage output of the energy harvesting system. Thus, some embodiments of the dual mode power supply 520 may include a rectifier, a low-pass filter (e.g., one or more capacitors), and/or voltage regulation/conditioning modules that may be similar in some respects to the rectifier 314, energy storage 316, and/or voltage regulator/conditioner 318 described in connection with FIG. 3 above.

The measurement and communication electronics 524 are shown and described in connection with FIG. 5A as a functional module that receives a DC supply voltage, obtains an amperometric current measurement measured through the working electrode, and then operates the antenna 522 to communicate the measured current. However, the measurement and communication electronics may include one or more of the functional modules shown and described in connection with FIG. 3 above, such as a sensor interface (e.g., a potentiostat), an antenna interface (e.g., a backscatter radiation modulator, one or more oscillators, etc.), and/or logic elements configured to cause the module 524 to function as described. Moreover, while the measurement and communication electronics are shown and described as a single physical module, it is noted that the measurement and communication electronics 524 can include a combination of one or more modules, or can be combined with other modules (e.g., rectifier, regulator and/or other related power supply modules) in a single physical implementation, such as an integrated circuit or chip.

In some examples, the dual mode power supply 520 is configured to switch between the standby mode and the active measurement mode based on signals received at the antenna 522. For example, the antenna 522, which can be an energy harvesting antenna similar to those described above in connection with FIGS. 2 and 3, can receive a low-level radio frequency radiation (e.g., radiated from an external reader), sufficient to generate a bias voltage across the sensor electrodes 502, 504. The dual mode power supply 520 can receive voltage fluctuations on the leads of the antenna 522 and generate one or both of a bias voltage (e.g., Vbias) or a DC supply voltage by harvesting the energy in the voltage fluctuations on the antenna leads. For example, the dual mode power supply 520 can rectify the radiation-induced voltage fluctuations and can filter (or otherwise regulate/condition) the voltage to generate a voltage output to supply to the sensor electrodes 502, 504 and/or the measurement and communication electronics 524.

In some embodiments, the dual mode power supply 520 is configured to detect the power of the received radiation and generate the DC supply voltage (e.g., to initiate the active measurement mode) only if the received radiation includes sufficient power to allow the DC supply voltage to be generated. Thus, the dual mode power supply 520 may automatically detect whether there is sufficient power in the received radiation to generate a DC supply voltage and generate the DC supply voltage only if enough power is available. In other words, the amount of power in the received radiation may, by itself, control the mode of operation of the dual mode power supply 520. On the other hand, in some embodiments, the received radiation can include indications embedded in the signal to initiate the active measurement mode or the standby bias mode. For example, the received radiation can include a binary indicator that can be interpreted by the dual mode power supply 520 (and/or related receiver electronics) to indicate whether the system 500 is in the standby bias mode or the active measurement mode. Thus, the system 500 may be operated to switch between standby bias mode and active measurement mode based on an embedded indicator in the received radiation, but without regard to the power of the received radiation. For instance, if the external reader (or other radio frequency radiation source) is located in close proximity, the received radiation may reach a high power level, but the radiation may still indicate that the system 500 is to be operated in the standby bias mode.

Operating the system 500 in the standby bias mode helpfully allows the system to circumvent costly energy consumption during a period of amperometric current stabilization that occurs immediately after first applying a bias voltage across the sensor electrodes 502, 504. While the bias voltage is applied, analytes present in the sensor region 501 electrochemically react at the working electrode 502 and are thereby electrochemically consumed. Thus, in a steady state operation, the analyte concentration in the sensor region 501 is balanced between the electrochemical consumption at the working electrode 502 and the diffusion of additional analyte into the sensor region 501 from surrounding areas. When the diffusion rate approximately balances the electrochemical consumption, the amperometric current reaches a stable value, which provides a good estimation of the analyte concentration at or near the sensor region 501. However, immediately after the bias voltage is first applied, the sensor system 500 is not in a steady state, and the electrochemical consumption rate is not balanced by the diffusion of additional analyte to the sensor region 501. Instead, immediately after the bias voltage is first applied, the sensor region 501 is filled with a relatively large amount of analyte, because the analyte is not being consumed at the working electrode 502, and so the initial amperometric current reading can be relatively greater than the eventual stable value. Once the relatively high concentration of analyte is consumed, the amperometric current stabilizes at a stable value where the electrochemical consumption balances analyte diffusion from surrounding areas.

As a result, some embodiments of the present disclosure provide techniques for avoiding sensor measurements obtained while the sensor is still stabilizing at its steady state amperometric current value. That is, techniques provided herein allow sensors to operate to only obtain measurements after the sensor is pre-charged with a bias voltage that allows the sensor to reach its steady state amperometric current value. In some embodiments, the sensor is pre-charged by applying a bias voltage to the sensor for a period of time sufficient to stabilize the amperometric current (e.g., in a standby bias voltage mode). The standby bias mode can immediately precede obtaining an amperometric current reading (e.g., in an active measurement mode). In such an example, the bias voltage is applied intermittently for a duration sufficient to achieve stabilization, and each application of the bias voltage is followed immediately by powering the measurement and communication electronics 524 to obtain a measurement and communicate the results. In some embodiments, the sensor electrodes are pre-charged substantially continuously to allow the sensor to continuously achieve its steady state level, but the measurement electronics are then powered only for short durations to intermittently obtain a measurement and communicate the results.

Figure 5B:
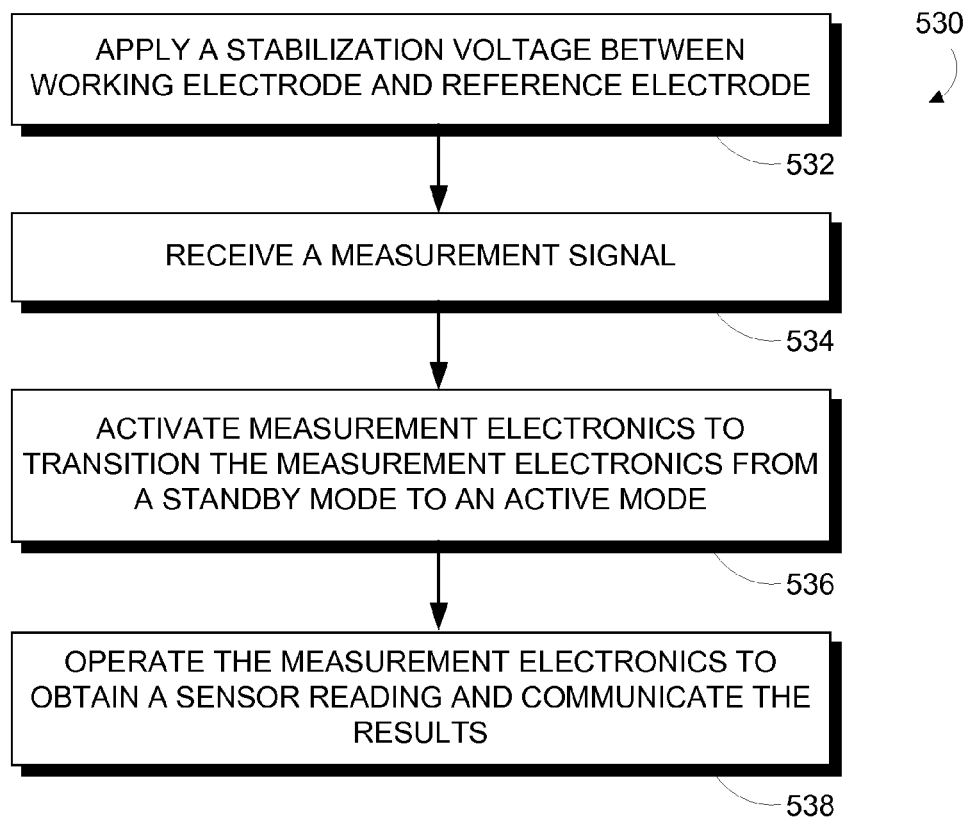
FIG. 5B is a flowchart of an example process for operating the example electrochemical sensor of FIG. 5A with a startup bias mode prior to obtaining a measurement.

In a measurement scheme where power is limited (e.g., an electrochemical sensor in an ophthalmic or implantable device that is inductively powered by harvested radiation), the system may be operated intermittently. FIG. 5B is a flowchart of an example process 530 for operating the example electrochemical sensor system 500 of FIG. 5A with a startup bias mode prior to obtaining a measurement. The dual mode power supply 520 applies a stabilization voltage (e.g., Vbias) between the working electrode 502 and the reference electrode 504 (532). While the bias voltage is being applied, the measurement and communication electronics 524 may be unpowered (e.g., no DC supply voltage is provided) or in a low-power state. The operation scheme of block 532 can be referred to herein as a standby bias voltage mode. The bias voltage can be applied for a sufficient duration to allow the amperometric current caused by the electrochemical reactions at the working electrode 502 to reach a steady state value. The duration may be referred to herein for convenience as a stabilization time (e.g., $t_{stab}$). In some embodiments, the application of the bias voltage can be initiated by receiving a signal from an external reader via the antenna 532 that indicates the standby bias mode (e.g., according to a power level of the received radiation and/or an embedded message in the signal).

A measurement signal can be received at the antenna 522 to indicate initiation of the active measurement mode (534). The measurement signal can be indicated by a message embedded (e.g., encoded) in a signal received at the antenna 522 and/or by a power level of the received radiation. For instance, the radio frequency radiation can increase to provide sufficient power to be harvested at the dual mode power supply 520 to allow for generation of both the bias voltage and the DC supply voltage to turn on the measurement and communication electronics 524. The received measurement signal in block 534 may thus cause the system 500 to activate the measurement and communication electronics 524 to transition the measurement and communication electronics 524 from the standby bias mode to the active measurement mode (536). For example, the measurement and communication electronics 524 can then be turned on by generating a DC supply voltage in the dual mode power supply 520 and providing the supply voltage to the measurement and communication electronics 524. Once transitioned to the active mode, the measurement and communication electronics 524 can measure the amperometric current through the working electrode 502 and communicate the sensor results through the antenna 522 (538). While the measurement and communication electronics 524 may be powered down (e.g., turned off) during the standby bias mode to minimize the power consumed during the standby bias mode, some embodiments may include the measurement and communication electronics 524 consuming a low level of power during the standby bias mode. The measurement and communication electronics 524 consume a greater amount of energy/power, while in the active measurement mode (e.g., as described in block 538) than in the standby mode (e.g., as described in block 532).

Figure 5C:
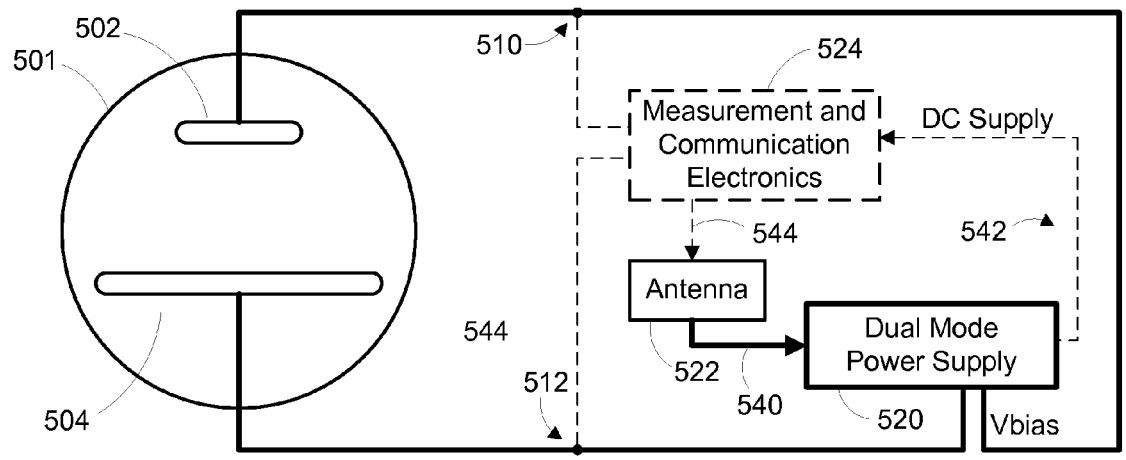
FIG. 5C is a functional block diagram of the example electrochemical sensor shown in FIG. 5A operating in standby mode.

FIG. 5C is a functional block diagram of the example electrochemical sensor shown in FIG. 5A operating in standby mode. For purposes of explanation only, the various modules and interconnections are shown illustrated with dashed lines to illustrate modules that are turned off (or in low-level power mode) and interconnections that are inactive (or in low-level power mode). Thus, in standby mode, the antenna 522 receives radiation, which generates low-level power input 540 to the dual mode power supply 520. The low-level power input 540 may include an embedded message instructing the system 500 to operate in standby mode or may include an amount of power that is insufficient to cause the system 500 to operate in the active measurement mode. The dual mode power supply 520 receives the low-level input 540 and rectifies and/or regulates the received input to generate the bias voltage (e.g., Vbias) that is output directly to the sensor electrodes 502, 504. The measurement and communication electronics 524 receive a power input 542 that is at a low level or zero level. Thus, measurement and communication electronics 524 are either turned off or in a standby, low-level power state.

Thus, in the standby mode the bias voltage is applied across the sensor electrodes 502, 504 without powering the measurement and communication electronics 524. The measurement and communication electronics 524 therefore do not modulate the antenna impedance (544), and the antenna 522 does not communicate any results via backscatter radiation. For clarity, the dashed modules and interconnects indicate inactive and/or low-level power mode modules and/or interconnects while the bold modules and interconnects indicate active modules and/or interconnects during the standby mode. In the standby mode, the dual mode power supply 520 receives energy from the antenna 522 and applies a bias voltage to the sensor electrodes 502, 504 (as indicated by the bold lines), but the measurement and communication electronics 524 are not operated to obtain a measurement of the amperometric currents or communicate the sensor results (as indicated by the dashed lines).

Figure 5D:
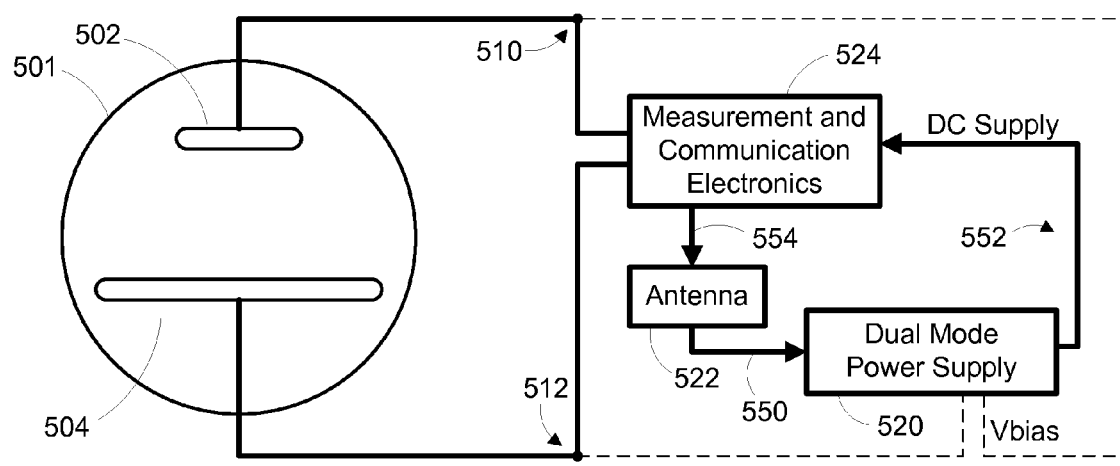
FIG. 5D is a functional block diagram of the example electrochemical sensor shown in FIG. 5A operating in active mode.

FIG. 5D is a functional block diagram of the example electrochemical sensor shown in FIG. 5A operating in an active measurement mode. Similar to the description in connection with FIG. 5C, the various modules and interconnects shown in FIG. 5D are shown in bold to indicate they are in an activated mode, while the dashed modules and interconnects indicate inactivated features. In the active measurement mode, the antenna 522 receives an active measurement mode signal that generates an active mode input 550 to the dual mode power supply. The active mode input 550 can be indicated by an embedded message in the received radiation and/or by a power level of the received radiation being sufficient to generate a DC supply voltage to power to the measurement and communication electronics 524. The active mode input 550 causes the dual mode power supply 520 to generate a DC supply voltage 552 that activates the measurement and communication electronics 524. The measurement and communication electronics 524 then operate the sensor electrodes 502, 504 to stabilize the voltage across the electrodes 502, 504 while measuring the amperometric current through the working electrode 502. The measurement and communication electronics 524 then modulate the antenna impedance (554) to cause the antenna 522 to communicate the sensor result (e.g., according to the modulation of the backscatter radiation from the antenna 522).

In some examples, the measurement and communication electronics 524 apply a voltage across the sensor electrodes 502, 504 that is different from the standby bias voltage Vbias. For example, the measurement and communication electronics 524 may apply a more accurate voltage across the sensor electrodes 502, 504 than the Vbias output of the dual mode power supply 520. Thus, while the voltage across the electrodes in the standby mode (e.g., Vbias) is generally approximately equal to the voltage across the electrodes 502, 504 while in the measurement mode (e.g., Vmeas), there may be a difference of approximately 20%. Generally, the voltage applied during the standby bias mode is selected to be sufficient to allow the amperometric current to reach a stable value, even if not as precise as the sensor voltage that is applied by the measurement and communication electronics 524 during the active measurement mode (e.g., Vmeas).

The measurement and communication electronics 524 may include, for example, a potentiostat configured to apply a voltage across the sensor electrodes 502, 504 while measuring the amperometric current through the working electrode 502. In the example illustrated in FIG. 5D, the dual mode power supply 520 is not used to provide the bias voltage during the active measurement mode (e.g., the bias voltage outputs from the dual mode power supply 520 may be disconnected or turned off), but this is only one embodiment provided for example purposes. In some examples, the bias voltage may be applied across the sensor electrodes 502, 504 by the measurement and communication electronics 524 and/ or the dual mode power supply 520 during the active measurement mode. For clarity, the dashed modules and interconnects indicate inactive and/or low-level power mode modules and/or interconnects while the bold modules and interconnects indicate active modules and/or interconnects during the standby mode. In the active measurement mode, the dual mode power supply 520 receives energy from the antenna 522 and provides a supply voltage to the measurement and communication electronics 524 (as indicated by the bold lines), and the measurement and communication electronics 524 obtain an amperometric current measurement through the working electrode 502 and communicate the results through the antenna 522.

Figure 6A:
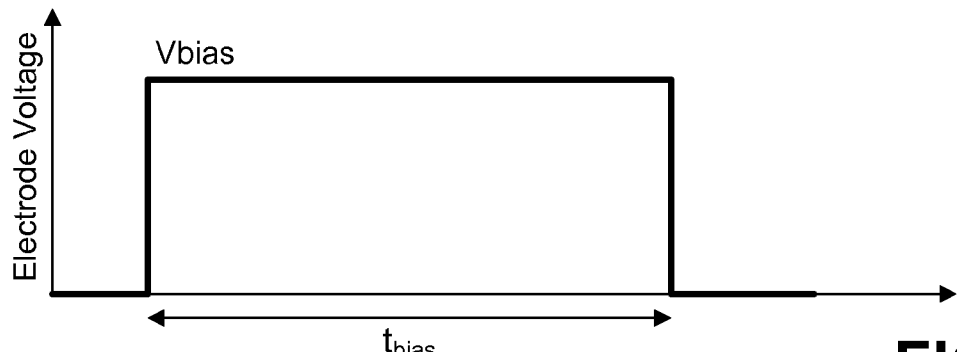
FIGS. 6A-6D illustrate sensor voltage, sensor current, electronics supply voltages, and power consumption for an example measurement cycle.
Figure 6B:
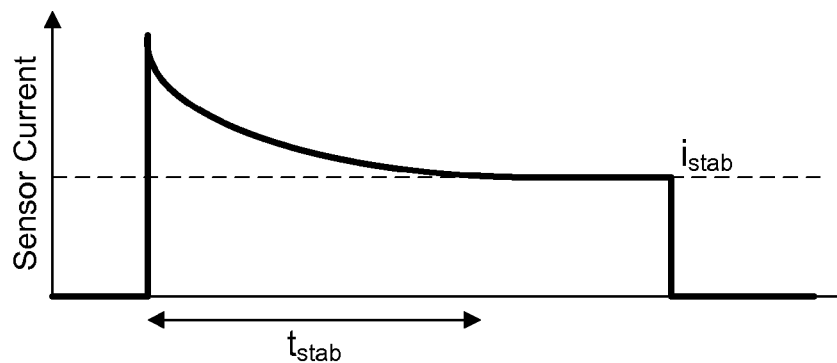

FIGS. 6A-6D illustrate sensor voltage, sensor current, electronics supply voltages, and power consumption for an example measurement cycle. The example shown in FIGS. 6A-6D illustrates an example operation scheme where the measurement and communication electronics are powered intermittently (i.e., non-continuously) to obtain a series of measurements over time without continuously powering the system. The measurement cycle is initiated by applying the bias voltage (e.g., Vbias) across the sensor electrodes 502, 504, which is indicated in FIG. 6A. The bias voltage is applied for a duration $t_{bias}$, which is the duration of the entire measurement cycle. The amperometric current due to electrochemical reactions at the working electrode 502 is shown in FIG. 6B, which shows an initial spike in the sensor current immediately after applying the bias voltage. The sensor current stabilizes at a value labeled $i_{stab}$ after a time $t_{stab}$. The value of $i_{stab}$ is the amperometric current value that reflects a steady state balance between analyte consumption by electrochemical reactions at the working electrode 502 and analyte diffusion into the sensor region 501. The duration $t_{stab}$ is the time required for the amperometric current to reach $i_{stab}$, and may be a pre-determined (e.g., pre-programmed) value and/or may be dynamically determined (e.g., by a processor in an external reader) based on the duty cycle of the measurement system (e.g., the fraction of time the system is in the measurement mode), previous and/or predicted values of $i_{stab}$, value of Vbias, duration of the immediately preceding standby bias voltage mode, etc.

Figure 6C:
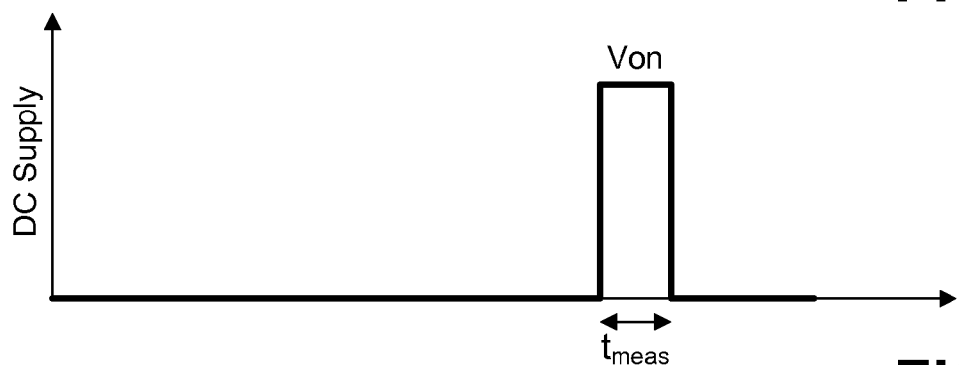

The supply voltage provided to the measurement and communication electronics 524 is shown in FIG. 6C. After $t_{stab}$ (e.g., after the amperometric current reaches a steady state value) the DC supply voltage is turned on (e.g., set to Von, a voltage sufficient to turn on the measurement and communication electronics 524). The DC supply voltage is turned on long enough to power the measurement and control electronics to obtain an amperometric current measurement and communicate the results (e.g., a time period $t_{meas}$). The duration of the measurement period $t_{meas}$ may be pre-determined (e.g., pre-programmed). The measurement mode (i.e., turning on the measurement and communication electronics 524) can be initiated in response to receiving a signal through the antenna 522 that includes an active measurement mode indicator.

Figure 6D:
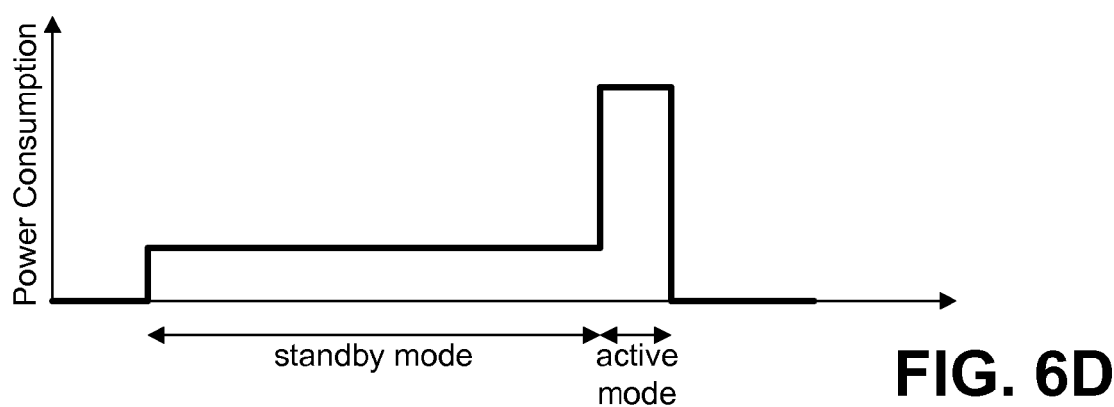

FIG. 6D shows the power consumption of the system 500 over the full measurement cycle, which includes both the standby mode and the active measurement mode. During the standby mode (e.g., while the bias voltage is applied and the amperometric current stabilizes without measuring or communicating sensor results), the power consumption is at a low level that reflects the dual mode power supply 520 generating the bias voltage, but not the DC supply voltage. During the active measurement mode (e.g., while the voltage Von is provided to the measurement and communication electronics), the power consumption is at a high level. In comparison to an operation scheme where the measurement and communication electronics are powered for the entire measurement cycle, including the stabilization period, rather than only following the standby bias voltage mode, the operation scheme including the standby bias voltage mode consumes much less power over time. In particular, in an operation scheme where the measurement and communication electronics are powered for the entire duration of the stabilization period, the power consumption of the system may be at the high level (indicated in FIG. 6D as the active mode) for the entire duration of the measurement cycle (e.g., the period $t_{bias}$ shown in FIG. 6A).

Figure 7A:
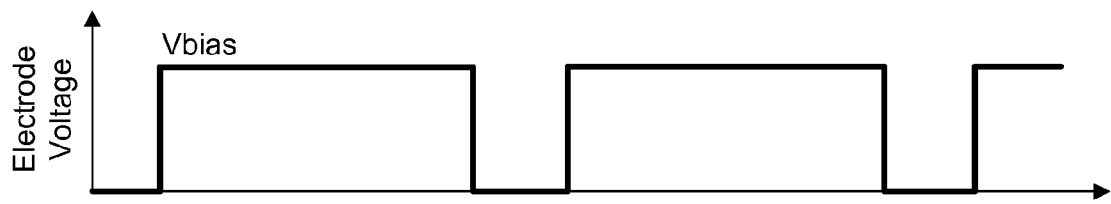
FIGS. 7A-7E illustrate sensor voltage, sensor current, electronics supply voltages, incident radiation, and power consumption for an example repeated measurement cycle.
Figure 7B:
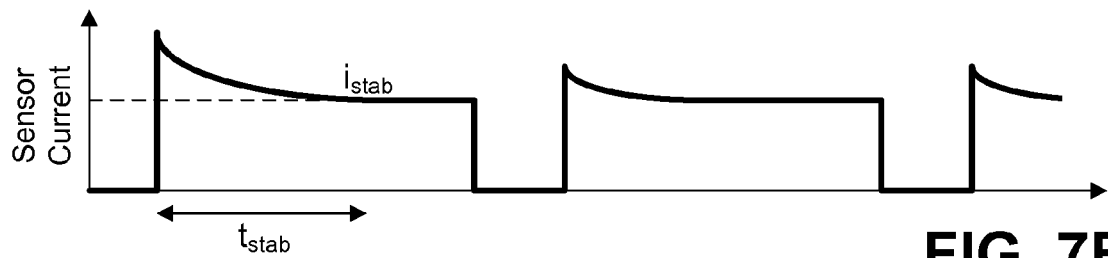
Figure 7C:
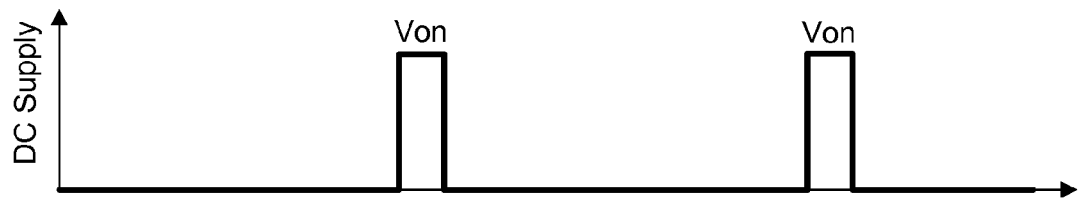
Figure 7D:
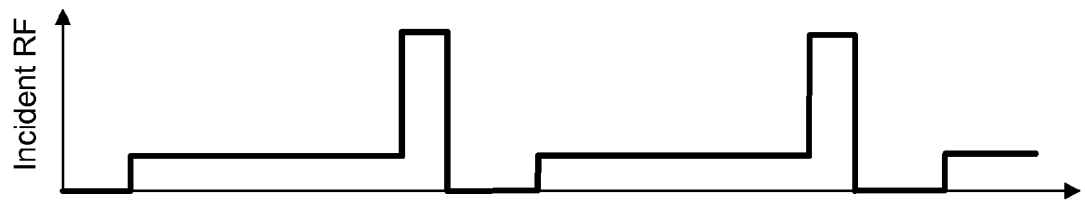
Figure 7E:
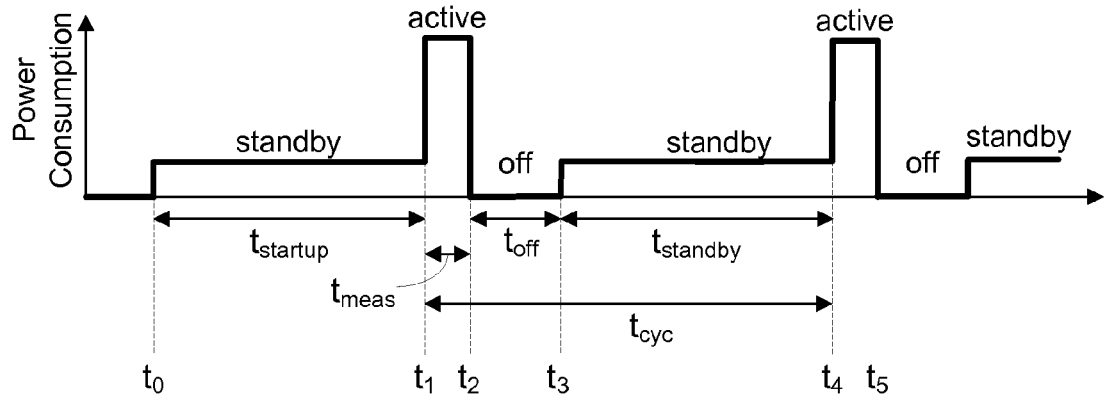

FIGS. 7A-7E illustrate sensor voltage, sensor current, electronics supply voltages, incident radiation, and power consumption for an example repeated measurement cycle. FIG. 7A shows the voltage applied across the sensor electrodes over time. FIG. 7B shows the sensor current over time. FIG. 7C shows the supply voltage provided to the measurement and communication electronics 524 over time. FIG. 7D shows the power of the incident radio frequency radiation over time that is needed to power the system by harvesting energy from the radiation. FIG. 7E shows the power consumption of the system over time when operated in the intermittent measurement scheme. Various time points in the operation scheme are labeled in FIG. 7E, but apply to all of the timing diagrams of FIGS. 7A-7E. At time t0 low level radiation is received at the antenna 522 sufficient to generate the bias voltage Vbias in the dual mode power supply 520. The dual mode power supply 520 accordingly generates the bias voltage and applies Vbias across the sensor electrodes 502, 504. The sensor current stabilizes at the current $i_{stab}$ over a period of time given by $t_{stab}$.

After a time period given by $t_{startup}$, the incident radiation increases to a high level at time t1. The high level radiation includes sufficient power that, when the energy is harvested by the dual mode power supply 520, the dual mode power supply can supply a DC supply voltage (e.g., the voltage Von) to the measurement and communication electronics 524. The high level radiation (shown in FIG. 7D) thus causes the system 500 to transition to the active measurement mode by causing the dual mode power supply 520 to generate a DC supply voltage to the measurement and communication electronics 524, which causes the measurement and communication electronics 524 to measure the amperometric current (i.e., the pre-stabilized current $i_{stab}$) through the working electrode 502 and communicate the results through the antenna 522 (e.g., by modulating the antenna impedance to adjust the backscatter radiation in a manner, that indicates the sensor result). The active measurement mode continues for a duration $t_{meas}$, until time t2, at which point the incident radiation goes to zero (as shown in FIG. 7D), and the system 500 can optionally turn off entirely (e.g., no bias voltage across the sensor electrodes 502, 504 and no supply voltage to the measurement and communication electronics 524). Thus, time t2 marks the end of a single measurement operation during which the system is put in standby mode to charge the bias voltage on the sensor electrodes and allow the current level to stabilize (standby mode from time t0 to t1) and then the measurement and control electronics and powered just long enough to obtain a measurement and communication the results (active measurement mode from time t1 to t2).

At time t3, which may occur a period $t_{off}$ after the time t2, a new measurement operation can be initiated by receiving low power-level radiation at the antenna (as shown in FIG. 7D). The low level radiation causes the system to enter standby mode. Thus, the dual mode power supply 520 applies a bias voltage across the sensor electrodes 502, 504 without powering the measurement and communication electronics 524. The system can undergo standby mode for a period $t_{standby}$, to allow the sensor current to stabilize. Then, at time t4, the active measurement mode is initiated once again when the incident radiation returns to a high power level, which causes the dual mode power supply 520 to provide a DC supply voltage to the measurement and communication electronics 524. In turn the measurement and communication electronics 524 measure the amperometric current through the working electrode 502 and communication the sensor result through the antenna 522. The active mode ends at time t5, and the intermittent measurement operation can continue thereafter by repeating the off mode, standby mode, and active measurement mode in turn to obtain a time series of amperometric sensor current readings.

The duration of the standby mode from time t0 to t1 (e.g., the duration $t_{startup}$) can be a pre-programmed duration for allowing the current level to stabilize when the timing of the previous application of the bias voltage and/or the previous current reading is unknown or uncertain. Thus, the value of $t_{startup}$ may be a relatively large duration that assumes a worst case for time required to achieve a stable amperometric current. However, the duration of the subsequent standby mode from time t3 to t4 (e.g., the duration $t_{standby}$) can be dynamically determined based on the duration of the off mode (e.g., the time $t_{off}$) and/or the value of the previously measured amperometric current (e.g., $i_{stab}$), and may optionally be shorter than $t_{startup}$. In some examples, an external reader that provides the incident radiation and receives the sensor results communicated back through the antenna may be configured to dynamically determine the duration of $t_{startup}$ (e.g., via a computing system associated with the external reader). For example, an external reader can control the system 500 to transition between the standby mode, active measurement mode, and/or off mode according to the radiation it emits toward the sensor system 500.

For example, when $t_{off}$ is large relative to the initial stabilization time, the system may substantially return to its initial state prior to the next measurement operation and the $t_{standby}$ may be approximately the same as $t_{startup}$. However, where $t_{off}$ is small relative to the initial stabilization time, the system may not fully return to its initial state prior to the next application of Vbias (e.g., at time t3) and so the duration required to achieve stabilization may be relatively less than the duration used initially. For example, where $t_{off}$ is small, the sensor region 501 may not be fully repopulated with analyte prior to initiation of the next measurement operation at time t3 and so relatively little time is required to allow the system to achieve steady state again. Moreover, the value of the previously measured amperometric current itself may additionally or alternatively be used to dynamically adjust the duration of the standby mode (e.g., the duration $t_{standby}$).

The duration of the full measurement cycle is shown as the time between subsequent measurements (e.g., the time $t_{cyc}$ between times t1 and t4). In some cases, the entire measurement cycle is repeated periodically with the time $t_{cyc}$ as the period such that each measurement is separated by the time $t_{cyc}$. However, the system 500 can be operated without repeating in a regular periodic fashion, such as where the time separation between subsequent measurements is dynamically adjusted or where measurements are performed according to available power (e.g., in an energy storage device powering the system to generate radiation to be harvested to initiate the measurement mode). In some examples, the system can be operated with a measurement mode duty cycle of less than 10%. For example, the duration of the measurement mode, $t_{meas}$, divided by the duration of the full measurement cycle, $t_{cyc}$, can be less than 10%. In some examples, the measurement mode duty cycle may be approximately 1%, or approximately 2%, or some other fraction depending on desired system performance.

Figure 8A:
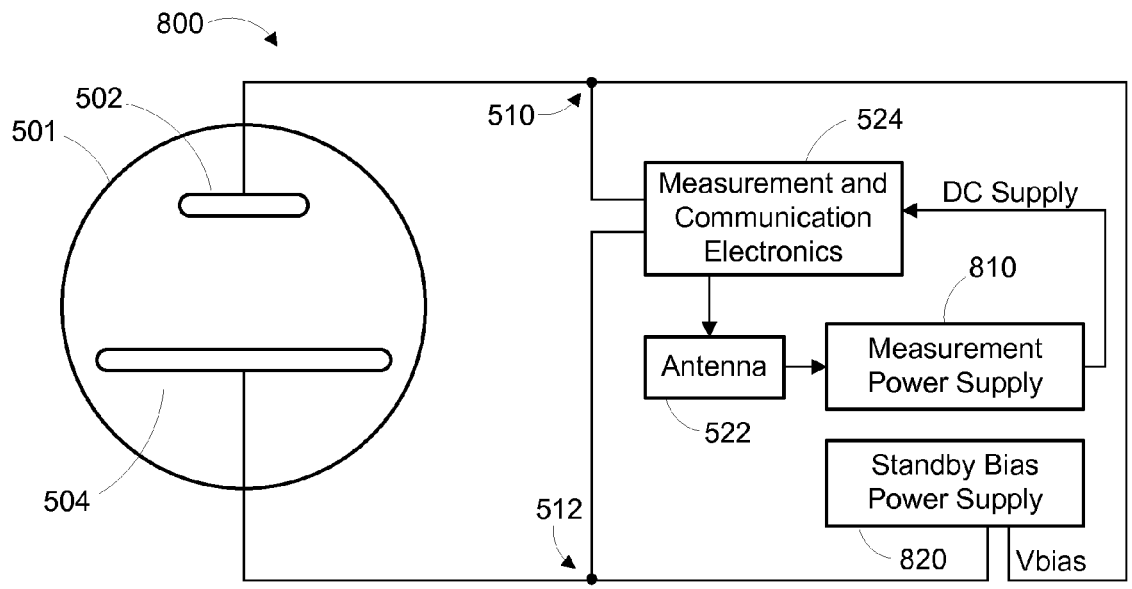
FIG. 8A is a functional block diagram of an example electrochemical sensor system including a measurement electronics power supply and a standby bias power supply.

FIG. 8A is a functional block diagram of an example electrochemical sensor system 800 including a measurement electronics power supply 810 and a standby bias power supply 820. By contrast with the system 500, rather than a dual mode power supply, the system 800 includes a measurement power supply 810 that operates by harvesting energy from incident radio frequency radiation and generating a DC supply voltage to turn on the measurement and communication electronics 524 and thereby cause the system 800 to obtain an amperometric current measurement through the working electrode 502 and communicate the sensor result through the antenna 522. The measurement power supply 810 may be a power supply that is dedicated to providing power to the measurement and control electronics 524. The measurement power supply 810 can generally be similar to the energy harvesting power supply system described in connection with FIG. 3 and may include one or more rectifiers, energy storage devices, and/or voltage regulators/conditioners configured to harvest energy in radio frequency electrical signals on leads of the antenna 522 caused by incident radiation and output a DC supply voltage to power the measurement and communication electronics 524.

In some embodiments, the measurement power supply 810 does not include an output for applying a bias voltage across the sensor electrodes 502, 504. However, the measurement and control electronics 524, which receive power from the measurement power supply 810, may apply a voltage across the sensor electrodes 502, 504 while obtaining an amperometric current measurement (e.g., similar to the operation of a potentiostat).

The standby bias power supply 820 generates the bias voltage Vbias and applies the bias voltage across the sensor electrodes 502, 504 during the standby mode to pre-charge the sensor electrodes 502, 504 and allow the amperometric current to stabilize at a steady state value prior to obtaining a measurement (e.g., with the measurement and communication electronics 524). In some examples, the standby bias power supply 820 can be an energy harvesting system that captures, rather than stores, energy in order to generate the bias voltage Vbias that is applied across the sensor electrodes 502, 504. In some examples, the standby bias power supply 820 can receive power from an auxiliary power source separate from the radio frequency energy harvesting antenna 522. For example, the standby bias power supply 820 can use a photovoltaic cell that generates a voltage in response to receiving incident light radiation. In some embodiments, the standby bias power supply 820 can also be powered from another energy harvesting source, such as an inertial motion energy harvesting system. Additionally or alternatively, the standby bias power supply 820 can be powered from incident radiation received at the antenna 522 (or another antenna dedicated to the standby bias power supply 820).

In some examples, the measurement and communication electronics 524 apply a voltage across the sensor electrodes 502, 504 that is different from the standby bias voltage Vbias generated by the standby bias power supply 820. For example, the measurement and communication electronics 524 may apply a more accurate voltage across the sensor electrodes 502, 504 than the Vbias output of the standby bias power supply 820. Thus, while the voltage across the electrodes in the standby mode (e.g., Vbias) is generally approximately equal to the voltage across the electrodes 502, 504 while in the measurement mode (e.g., Vmeas), there may be a difference of approximately 20%. Generally, the voltage applied during the standby bias mode is selected to be sufficient to allow the amperometric current to reach a stable value, even if not as precise as the sensor voltage that is applied by the measurement and communication electronics 524 during the active measurement mode (e.g., Vmeas).

Figure 8B:
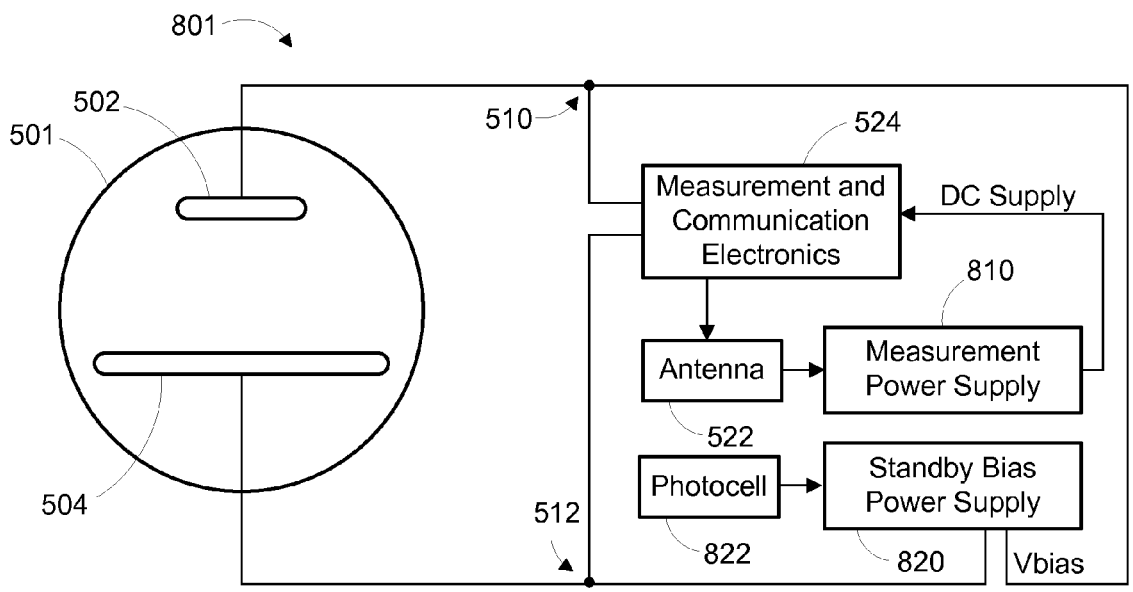
FIG. 8B is a functional block diagram of an example embodiment where the standby bias power supply includes a photovoltaic cell.

FIG. 8B is a functional block diagram of an example embodiment where the standby bias power supply 820 includes a photovoltaic cell 822. As shown in FIG. 8B, a photovoltaic cell 822 provides a voltage output to the standby bias power supply 820. Moreover, the photovoltaic cell can be included in the standby bias power supply 820. In some embodiments, the standby bias power supply 820 may comprise a photovoltaic cell (e.g., the photovoltaic cell 822) that outputs a voltage Vbias across two terminals in response to incident light radiation. The two terminals of the photovoltaic cell 822 can then be connected to the two sensor electrodes 502, 504 (e.g., via the nodes 510, 512) to apply the bias voltage across the sensor electrodes and thereby allow the electrochemical sensor to achieve stabilization. The photovoltaic cell 822 can be, for example, a solar cell or a combination of such solar cells. The photovoltaic cell can be activated in response to the receipt of light at a range of different wavelengths, such as visible light, ultraviolet light, near infrared light, etc. Although, a particular photovoltaic cell may be configured to be activated at a selected range of wavelengths as desired. In an application where the electrochemical sensor is included in an eye-mountable device (e.g., embedded in a transparent polymeric material configured to be contact-mounted to an eye surface) the photovoltaic cell 822 can be embedded in the eye-mountable device and can receive incident light radiation that is transmitted through the eye-mountable device.

In some examples, the standby bias power supply 820 can operate to apply a bias voltage Vbias to the sensor electrodes 502, 504 substantially continuously and thereby keep the system 800 substantially continuously pre-charged in a state where the amperometric current is stabilized. Thus, the standby bias power supply 820 may be operated substantially independent of the incident radiation received at the antenna 522. For example, the standby bias power supply 820 can apply the bias voltage to the sensor electrodes 502, 504 whenever the standby bias power supply 820 receives a power input (e.g., incident light radiation, inertial motion, etc.). Thus, the system 800 can be used to obtain a time series of amperometric current measurements by intermittently powering the measurement and communication electronics 524 to measure the amperometric current and communicate the results. Where the standby bias power supply 820 is operated substantially continuously, the system 800 may intermittently receive radio frequency radiation (at the antenna) to initiate an active measurement mode. Energy from the received radio frequency radiation can be harvested by the measurement power supply 810 to generate a DC supply voltage to power the measurement and communication electronics 524, and the measurement and communication electronics 524 can measure the amperometric current through the working electrode 502 and communicate the measurement result through the antenna 522 (e.g., by modulating the antenna impedance to adjust the backscatter radiation).

Figure 8C:
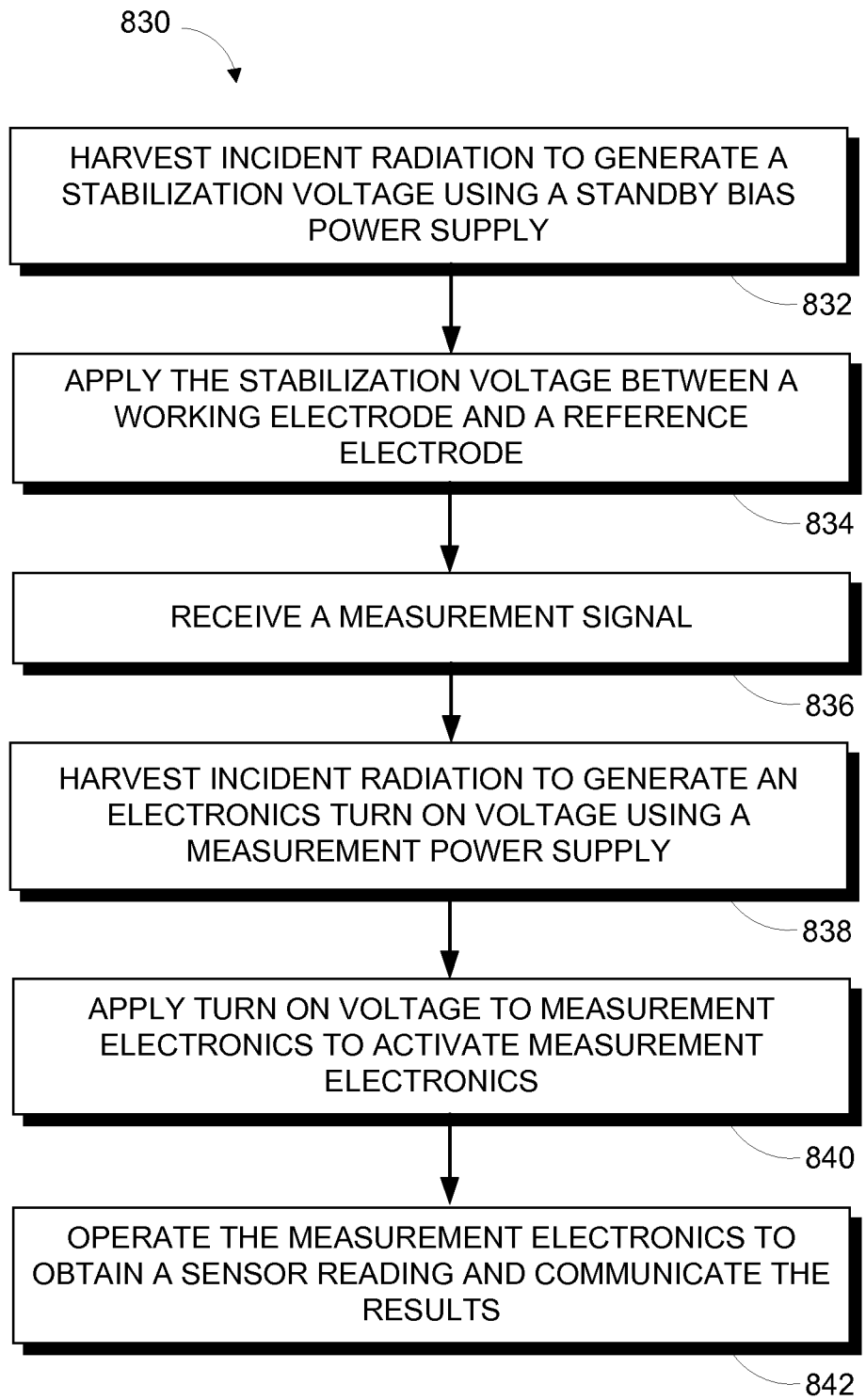
FIG. 8C is a flowchart of an example process for operating the example electrochemical sensor of FIG. 8A with a startup bias mode prior to obtaining a measurement.

FIG. 8C is a flowchart of an example process 830 for operating the example electrochemical sensor of FIG. 8A with a startup bias mode prior to obtaining a measurement. Energy is harvested from incident radiation to generate a stabilization voltage (or bias voltage) using the standby bias power supply 820 (832). The standby bias power supply 820 can harvest energy from incident light radiation, from an inertial energy harvesting system, etc. The stabilization voltage (or bias voltage) is applied between the working electrode 502 and the reference electrode 504 (834). The stabilization voltage is a voltage sufficient to cause the analyte in the sensor region 501 to electrochemically react at the working electrode and thereby generate an amperometric current. A measurement signal indicating the initiation of an active measurement mode is received (836). For example, the measurement signal can be radio frequency radiation with sufficient energy to operate the measurement power supply 810 to generate a DC supply voltage by harvesting the energy in the received radiation. The measurement signal can additionally or alternatively include a message embedded in the received radiation that instructs the sensor system 800 (e.g., via associated receiver electronics) to initiate the active measurement mode.

Incident radio frequency radiation is harvested by the measurement power supply 810 to generate a DC supply voltage sufficient to turn on the measurement and communication electronics 524 (838). For example, the measurement power supply 810 can output a voltage Von that causes the measurement and communication electronics 524 to transition from a standby mode to an active measurement mode. The turn on voltage (e.g., Von) is applied to the measurement and communication electronics to activate the measurement electronics (840). The measurement and communication electronics 524 are then operated to obtain a sensor reading and communicate the results (842). For example, the measurement and communication electronics can measure the amperometric current through the working electrode 502 and communicate the results through the antenna 522. In some examples, the measurement and communication electronics 524 can be turned off while in the standby mode and turn on upon receiving the DC supply from the measurement power supply 810. Generally, the measurement and communication electronics 524 consume less power in the standby mode (or idle mode) than in the active measurement mode. Thus, the process 830 allows for obtaining a time series of amperometric current measurements without continuously powering the measurement and communication electronics 524.

Figure 9A:
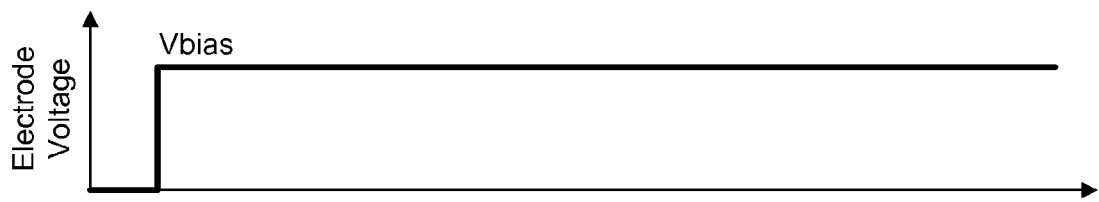
FIGS. 9A-9E illustrate sensor voltage, sensor current, electronics supply voltages, incident radiation, and power consumption for an example repeated measurement cycle.
Figure 9B:
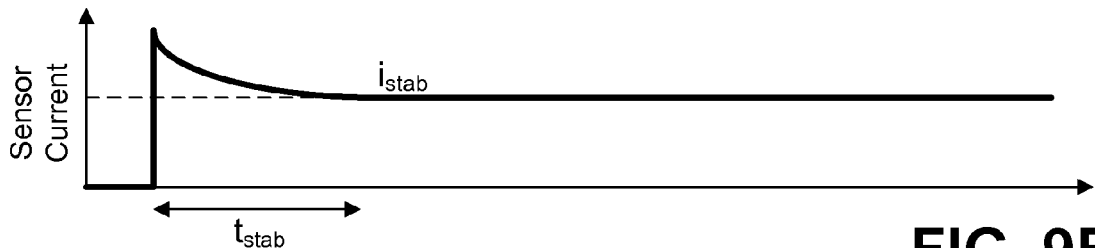
Figure 9C:
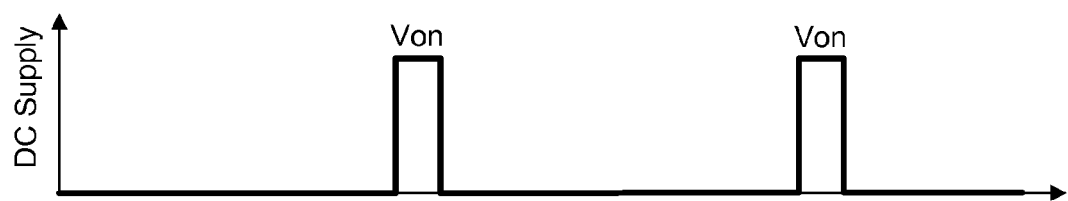
Figure 9D:
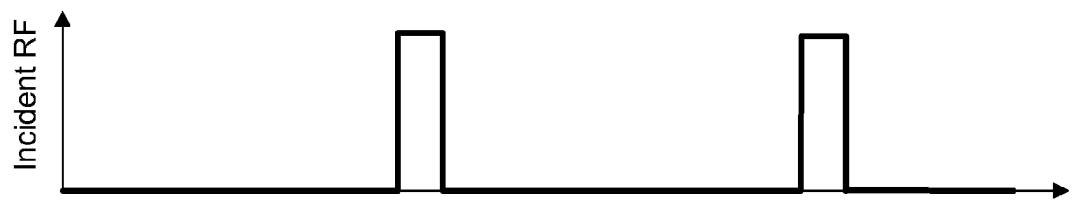
Figure 9E:
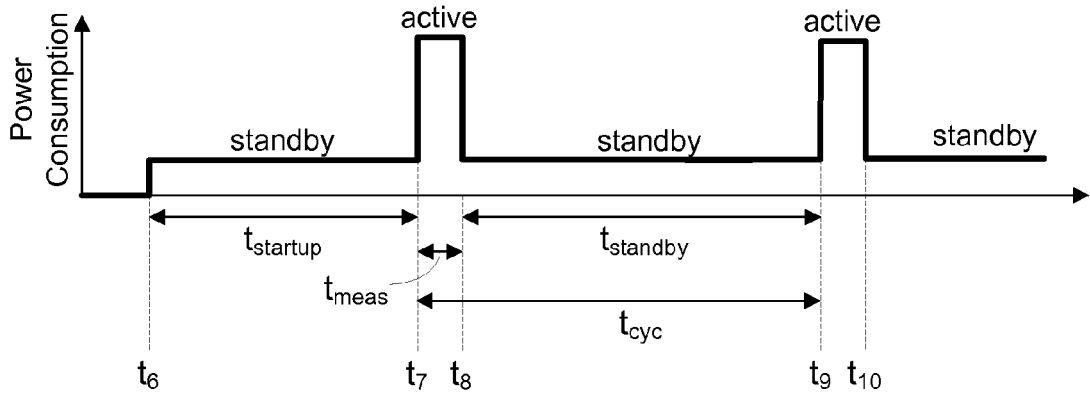

FIGS. 9A-9E illustrate sensor voltage, sensor current, electronics supply voltages, incident radiation, and power consumption for an example repeated measurement cycle using the example electrochemical system 800 shown in FIG. 8A. FIG. 9A shows the voltage applied across the sensor electrodes over time. FIG. 9B shows the sensor current over time. FIG. 9C shows the supply voltage provided to the measurement and communication electronics 524 over time. FIG. 9D shows the power of the incident radio frequency radiation over time that is needed to power the system by harvesting energy from the radiation. FIG. 9E shows the power consumption of the system over time when operated in the intermittent measurement scheme. Various time points in the operation scheme are labeled in FIG. 9E, but apply to all of the timing diagrams of FIGS. 9A-9E.

At time t6 the bias voltage Vbias is generated by the standby bias power supply 820 (e.g., by energy harvested with a photovoltaic cell and/or inertial energy harvesting system) and applied across the sensor electrodes 502, 504. The sensor current stabilizes at the current $i_{stab}$ over a period of time given by $t_{stab}$. After a time period $t_{startup}$, which is greater than $t_{stab}$, the system 800 can transition to the active measurement mode at time t7. For example, at time t7, the radio frequency radiation received at the antenna 522 can increase to a high power level and can optionally include an embedded message instructing the system 800 to transition to the active measurement mode. For example, the high power level radio frequency radiation can be emitted from an external reader configured to operate the electrochemical sensor system 800. The measurement mode power supply 810 can harvest energy from the incident radio frequency radiation to generate a turn on voltage (e.g., the voltage Von) and apply the turn on voltage to the measurement and communication electronics 524. During the period from t7 to t8, with duration $t_{meas}$, the measurement and communication electronics 524 can measure the amperometric current through the working electrode 502 and communicate the sensor result through the antenna 522.

Following the duration $t_{meas}$, the incident radio frequency radiation can return to a low power level and the measurement power supply 810 can cease supplying the DC power supply to the measurement and communication electronics 524, so as to cause the system to return to the standby mode. Following a duration $t_{standby}$, the active measurement mode is activated again at time t9, and the system 800 obtains and communicates another amperometric current measurement. The bias voltage Vbias can be substantially continuously applied to the sensor electrodes to keep the sensor constantly pre-charged and ready to obtain and communicate a measurement. The active measurement mode can be repeated intermittently to obtain a time series of measurements. In some examples, the active measurement mode is repeated periodically with a period $t_{cyc}=t_{meas}+t_{standby}$. Alternatively, the measurement mode can be repeated with an irregular period, and can optionally be repeated with a period that is dynamically adjusted (e.g., based on the rate of change of subsequent amperometric current readings). In some examples, the system can be operated with a measurement mode duty cycle of less than 10%. For example, the duration of the measurement mode, $t_{meas}$, divided by the duration of the full measurement cycle, $t_{cyc}$, can be less than 10%. In some examples, the measurement mode duty cycle may be approximately 1%, or approximately 2%, or some other fraction depending on desired system performance.

In some examples, either of the electrochemical sensor systems (e.g., the system 500 and/or the system 800) can be operated to verify that the sensor has achieved stabilization during each active measurement mode. For example, rather than performing a single amperometric current reading during each active measurement mode (e.g., during the period $t_{meas}$), the system can be obtain two (or more) measurements and communicate both results. The external reader can then compare the two sensor results to determine whether the amperometric current was at a stable value during the measurement. For example, where two (or more) amperometric current readings are near the same value, the external reader may conclude that the system was at a stable current value, and therefore the current readings are reliable indicators of the analyte concentration. On the other hand, where two (or more) amperometric current readings evidence non-stable trend in the current (e.g., a downward trend approaching a stable value) then the external reader may conclude the system was not at a stable current value, and therefore the current readings are not reliable indicators of the analyte concentration. In such an example, the external reader may optionally signal the electrochemical sensor to immediately obtain an additional measurement (e.g., by immediately initiating the standby bias mode) rather than wait for a pre-determined period of time typically taken between subsequent measurements.

Figure 10A:
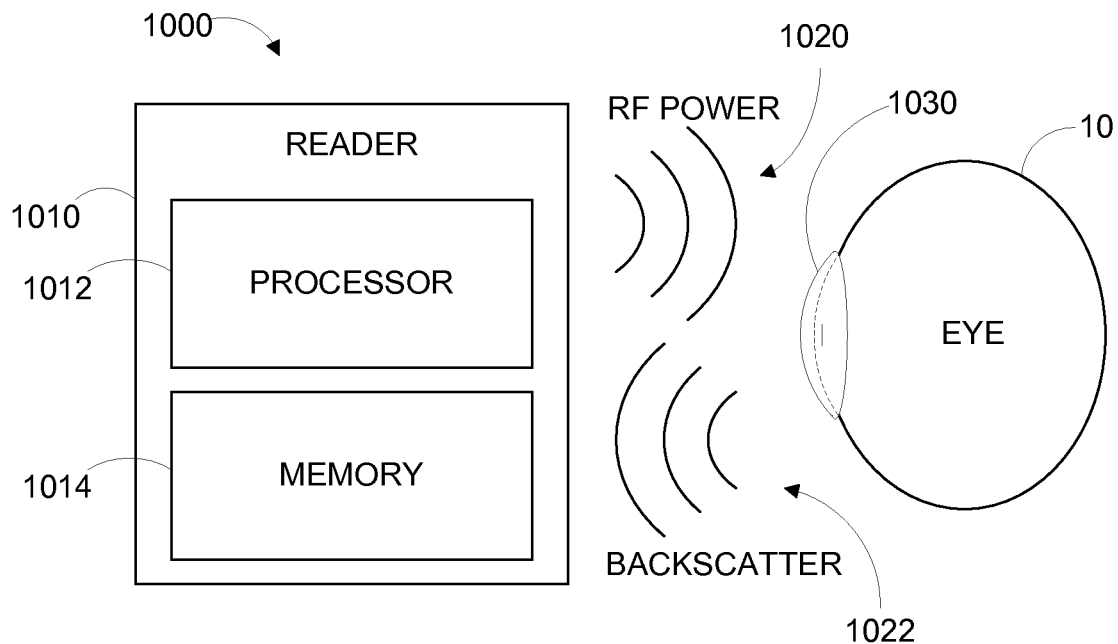
FIG. 10A is a block diagram of an ophthalmic electrochemical sensor system operated by an external reader to obtain a series of amperometric current measurements over time.

FIG. 10A is a block diagram of a system 1000 with an ophthalmic electrochemical sensor 1030 operated by an external reader 1010 to obtain a series of amperometric current measurements over time. The ophthalmic electrochemical sensor 1030 is included in an eye-mountable device configured to be contact-mounted over a corneal surface of an eye 10. The ophthalmic electrochemical sensor 1030 can be operated to be transitioned into an active measurement mode in response to receiving a measurement signal from the external reader 1010.

The external reader 1010 includes a processing system 1012 and a memory 1014. The processing system 1012 can be a computing system that executes software stored in the memory 1014 to cause the system 1000 to operate as described herein to obtain a time series of measurements (e.g., by intermittently transmitting a measurement signal to cause the ophthalmic electrochemical sensor 1030 to obtain a measurement and communicate the results as shown in connection with FIGS. 7 and 9). The external reader 1010 can also include an antenna (not shown) for transmitting radio frequency radiation 1020 to be harvested by the ophthalmic electrochemical sensor 1030. The external reader 1010 can also receive indications of sensor results 1022 transmitted back to the reader by backscatter radiation. For example, the antenna impedance of the ophthalmic electrochemical sensor 1030 can be modulated in accordance with the sensor result such that the backscatter radiation 1022 indicates the sensor results. The external reader 1010 can also use the memory 1014 to store indications of amperometric current measurements communicated by the ophthalmic electrochemical sensor 1030. The external reader 1010 can thus be operated to intermittently power the ophthalmic electrochemical sensor 1030 so as to obtain a time series of amperometric current measurements.

Figure 10B:
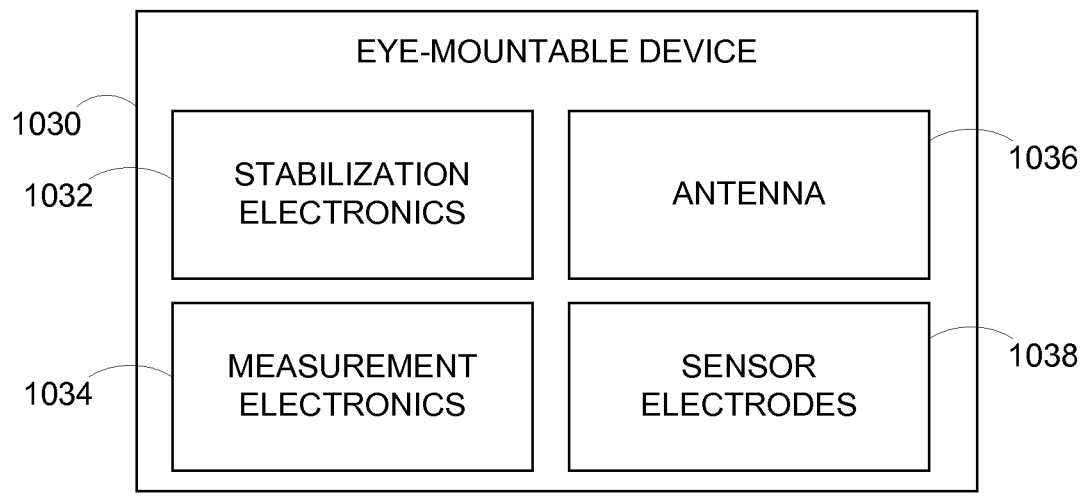
FIG. 10B is a block diagram of the ophthalmic electrochemical sensor system described in connection with FIG. 10A.

FIG. 10B is a block diagram of the ophthalmic electrochemical sensor 1030 described in connection with FIG. 10A. The ophthalmic electrochemical sensor 1030 can be configured to operate similar to the system 500 and/or the system 800 described in connection with FIGS. 5-9 above. Thus, the ophthalmic electrochemical sensor 1030 can include energy harvesting systems for harvesting energy from incident radiation (and/or other sources) to generate bias voltage to apply across sensor electrodes during a standby mode. The ophthalmic electrochemical sensor can also be configured to generate power from incident radiation to power measurement and communication electronics in response to receiving a measurement signal indicating initiation of an active measurement mode.

The ophthalmic electrochemical sensor 1030 can include stabilization electronics 1032, measurement electronics 1034, an antenna 1036, and sensor electrodes 1038. The stabilization electronics 1032 can be configured to apply a stabilization voltage (e.g., the bias voltage Vbias) between the sensor electrodes 1038 while the ophthalmic electrochemical sensor 1030 is operating in the standby mode (or stabilization mode). Thus, the stabilization electronics 1032 may include the dual mode power supply 520 or an auxiliary power supply such as the standby bias power supply 820 described above, for example. The measurement electronics 1034 are configured to measure the amperometric current through the working electrode of the sensor electrodes 1038 and communicate the measured amperometric current through the antenna 1036. The measurement electronics 1034 can also be configured to harvest energy from incident radio frequency radiation via the antenna 1036 and use the harvested energy to power the measurement and communication of the amperometric current. Thus, the measurement electronics may include the measurement and communication electronics 524, the measurement power supply 810, and/or the dual mode power supply 520 described above.

Figure 10C:
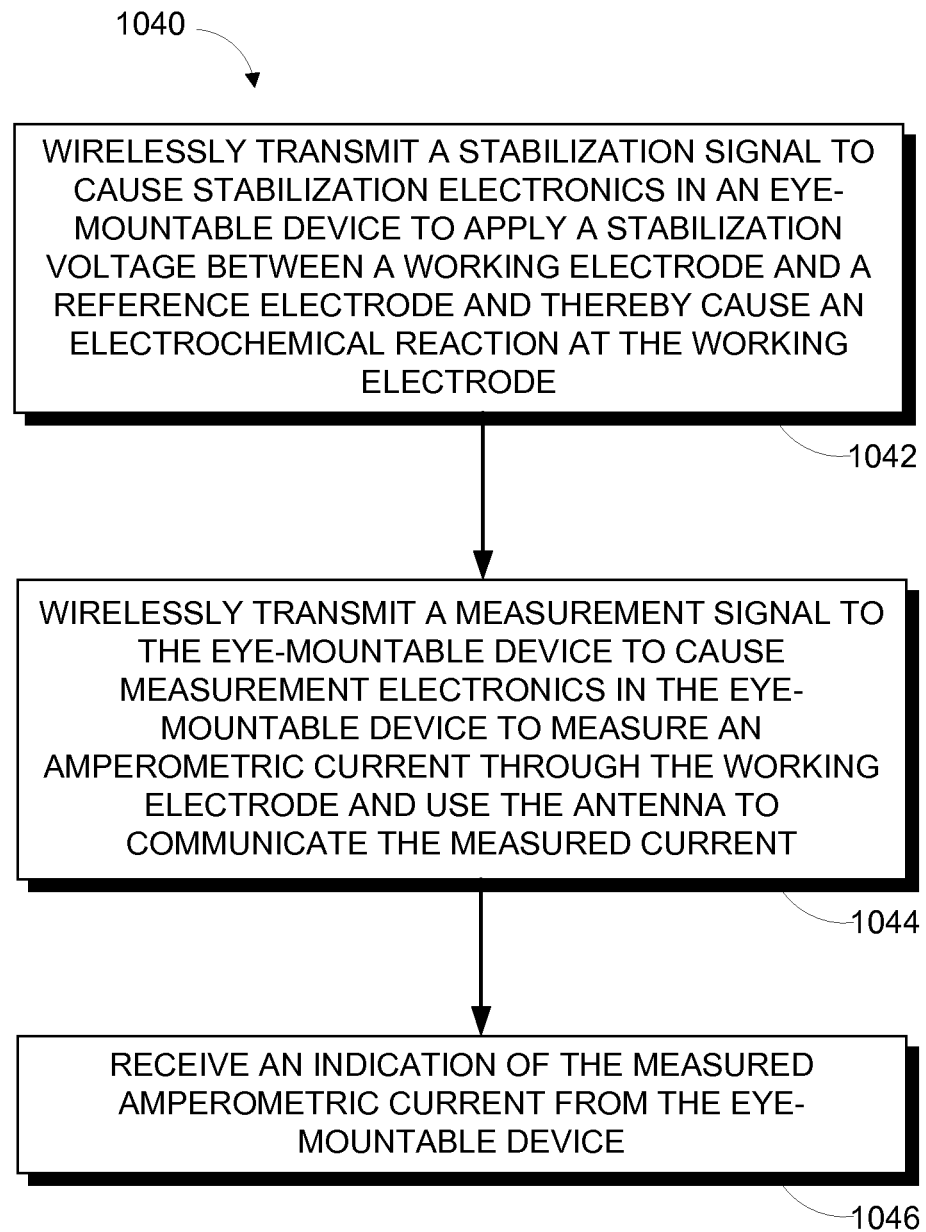
FIG. 10C is a flowchart of an example process for operating the ophthalmic electrochemical sensor system shown in FIG. 10A.

FIG. 10C is a flowchart of an example process 1040 for operating the ophthalmic electrochemical sensor system shown in FIG. 10A. A stabilization signal is transmitted from the external reader 1010 to the ophthalmic electrochemical sensor 1030 (1042). The stabilization signal can include radio frequency radiation with a low power level that is sufficient to cause the stabilization electronics 1032 in the ophthalmic electrochemical sensor 1030 to apply a stabilization voltage (e.g., the voltage Vbias) between the sensor electrodes 1038 and thereby cause an analyte of interest to electrochemically react at the working electrode, which reactions generate an amperometric current. The stabilization signal transmitted in block 1042 can thus cause the ophthalmic electrochemical sensor to reach a stable amperometric current value. In some examples, the stabilization signal may be substantially continuously transmitted for a duration sufficient to allow the electrochemical sensor to reach a steady state (e.g., such that the amperometric current is at a stable value).

A measurement signal is then wirelessly transmitted from the external reader 1010 to the ophthalmic electrochemical sensor 1030 (1044). The measurement signal can include radio frequency radiation with a high power level that is sufficient to cause the measurement electronics 1034 in the ophthalmic electrochemical sensor 1030 to measure an amperometric current through the working electrode and use the antenna to communicate the measured amperometric current. In some examples, the measurement signal is transmitted immediately following the end of transmission of the stabilization signal to cause the ophthalmic electrochemical sensor to transition immediately from the stabilization mode (or standby mode) to the measurement mode. An indication of the measured amperometric current is received back at the external reader (1046). The measured amperometric current may be indicated by modulating the impedance of the antenna 1036 in the ophthalmic electrochemical sensor 1030 such that the modulation in the antenna impedance can be detected by the external reader 1010 and mapped to an associated amperometric current reading. For example, the impedance modulation may be detected via the backscatter radiation 1022 from the ophthalmic electrochemical sensor.

Figure 11:
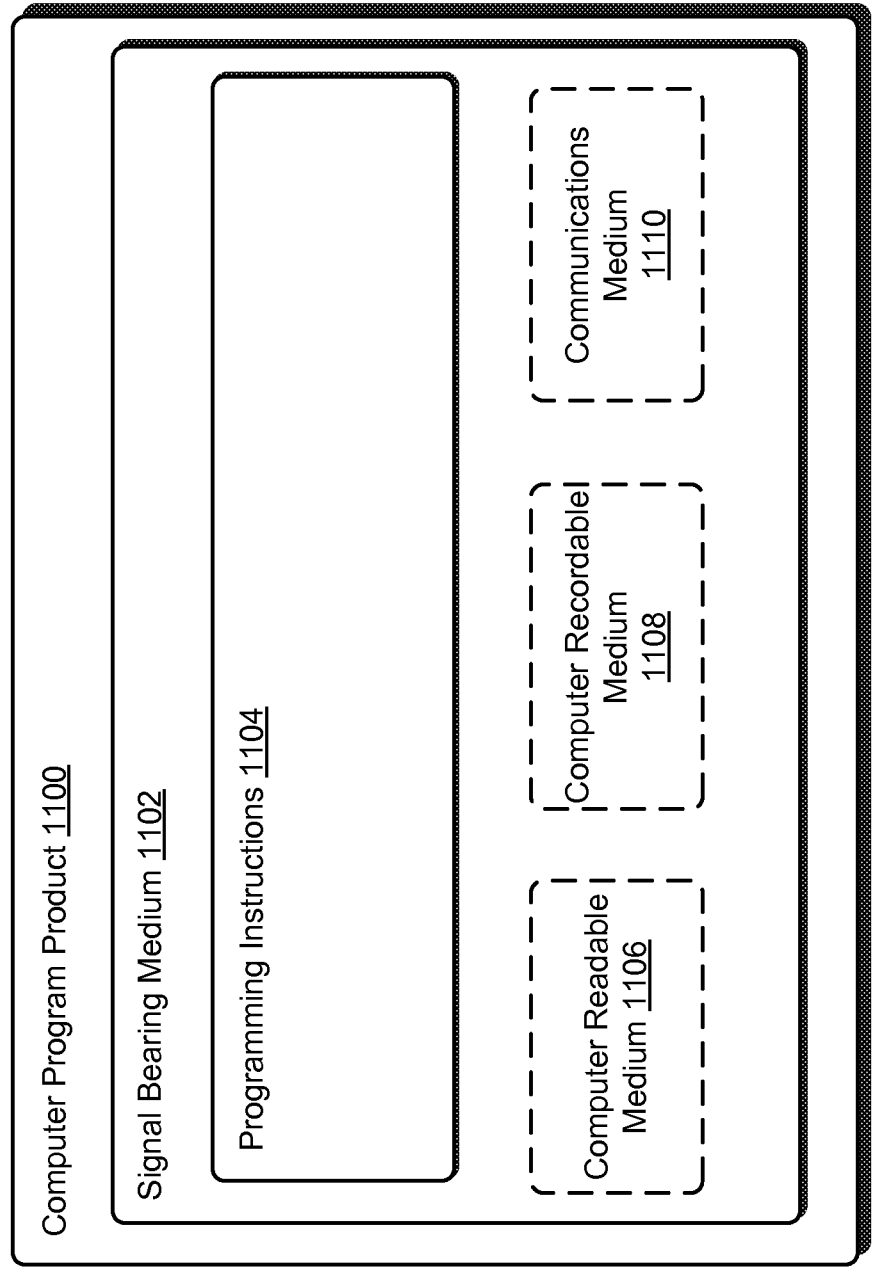
FIG. 11 depicts a computer-readable medium configured according to an example embodiment.

FIG. 11 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture (e.g., the instructions 184 stored on the memory storage 182 of the external reader 180 of the system 100). FIG. 11 is a schematic illustrating a conceptual partial view of an example computer program product that includes a computer program for executing a computer process on a computing device, arranged according to at least some embodiments presented herein.

In one embodiment, the example computer program product 1100 is provided using a signal bearing medium 1102. The signal bearing medium 1102 may include one or more programming instructions 1104 that, when executed by one or more processors may provide functionality or portions of the functionality described above with respect to FIGS. 1-10. In some examples, the signal bearing medium 1102 can be a non-transitory computer-readable medium 1106, such as, but not limited to, a hard disk drive, a Compact Disc (CD), a Digital Video Disk (DVD), a digital tape, memory, etc. In some implementations, the signal bearing medium 1102 can be a computer recordable medium 1108, such as, but not limited to, memory, read/write (R/W) CDs, R/W DVDs, etc. In some implementations, the signal bearing medium 1102 can be a communications medium 1110, such as, but not limited to, a digital and/or an analog communication medium (e.g., a fiber optic cable, a waveguide, a wired communications link, a wireless communication link, etc.). Thus, for example, the signal bearing medium 1102 can be conveyed by a wireless form of the communications medium 1110.

The one or more programming instructions 1104 can be, for example, computer executable and/or logic implemented instructions. In some examples, a computing device such as the processor-equipped external reader 180 of FIG. 1 is configured to provide various operations, functions, or actions in response to the programming instructions 1104 conveyed to the computing device by one or more of the computer readable medium 1106, the computer recordable medium 1108, and/or the communications medium 1110.

The non-transitory computer readable medium 1106 can also be distributed among multiple data storage elements, which could be remotely located from each other. The computing device that executes some or all of the stored instructions could be an external reader, such as the reader 180 illustrated in FIG. 1, or another mobile computing platform, such as a smartphone, tablet device, personal computer, etc. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
   applying a stabilization voltage between a working electrode and a reference electrode in an eye-mountable device, wherein the stabilization voltage is sufficient to cause an analyte to undergo an electrochemical reaction at the working electrode;
   while the stabilization voltage is being applied, wirelessly receiving a measurement signal at an antenna in the eye-mountable device;
   responsive to receiving the measurement signal, activating measurement electronics in the eye-mountable device to transition the measurement electronics from a standby mode to an active mode, wherein the measurement electronics consume more power in the active mode than in the standby mode; and
   during the active mode, operating the measurement electronics to (i) measure an amperometric current through the working electrode, wherein the amperometric current is related to the analyte, and (ii) wirelessly communicate the measured amperometric current via the antenna.

2. The method according to claim 1, further comprising:
   after wirelessly communicating the measured amperometric current via the antenna, de-activating the measurement electronics to transition the measurement electronics from the active mode to the standby mode.

3. The method according to claim 1, further comprising intermittently activating the measurement electronics to wirelessly communicate a series of amperometric current values measured through the working electrode, wherein each of the amperometric current values is measured following a stabilization period during which the stabilization voltage is applied to allow current through the working electrode caused by the stabilization voltage to reach a stable value prior to measurement.

4. The method according to claim 3, wherein the measurement electronics are intermittently activated with a duty cycle of less than 10 percent.

5. The method according to claim 1, further comprising:
   during the active mode, applying a measurement voltage between the working electrode and the reference electrode, wherein the measurement voltage generates the amperometric current.

6. The method according to claim 5, wherein the stabilization voltage is supplied by an auxiliary power supply and the measurement voltage is supplied by a primary power supply.

7. The method according to claim 5, wherein the stabilization voltage and the measurement voltage are approximately equal.

8. The method according to claim 5, wherein the stabilization voltage is within 20 percent of the measurement voltage.

9. The method according to claim 1, further comprising:
   during the active mode, harvesting energy from radio frequency (RF) radiation received at the antenna to power the measurement electronics.

10. The method according to claim 1, further comprising:
    applying the stabilization voltage during a stabilization period, wherein the stabilization period has a duration sufficient to allow current through the working electrode to reach a stable value prior to activating the control electronics such that the amperometric current measured by the measurement electronics is not affected by transient variations.

11. The method according to claim 1, wherein the received measurement signal includes radio frequency radiation for powering an energy harvesting power supply, and wherein the method further comprises:
    rectifying electrical signals on the antenna caused by the received radio frequency radiation to thereby generate a supply voltage; and
    applying the generated supply voltage to the measurement electronics to power the measurement electronics.

12. The method according to claim 1, further comprising:
    prior to receiving a subsequent measurement signal, operating the measurement electronics in the active mode to measure a second amperometric current value through the working electrode and wirelessly communicate the second amperometric current value via the antenna.

13. A method comprising:
    during a stabilization period, wirelessly transmitting, by a reader, a stabilization signal to an eye-mountable device comprising a working electrode, stabilization electronics, measurement electronics, and an antenna, wherein the stabilization signal is configured to cause the stabilization electronics to apply a stabilization voltage between the working electrode and the reference electrode, wherein the stabilization voltage is sufficient to cause an analyte to undergo an electrochemical reaction at the working electrode;
    during a measurement period following the stabilization period, wirelessly transmitting, by the reader, a measurement signal to the eye-mountable device, wherein the measurement signal is configured to (i) cause the measurement electronics to measure an amperometric current through the working electrode, wherein the amperometric current is related to the analyte, (ii) cause the measurement electronics to wirelessly communicate the measured amperometric current via the antenna, and (iii) supply power for powering the measurement electronics; and
    receiving, by the reader, an indication of the measured amperometric current wirelessly communicated from the eye-mountable device.

14. The method according to claim 13, further comprising:
during an idle period following the measurement period, the reader discontinuing transmission of wireless signals to the eye-mountable device.

15. The method according to claim 13, further comprising:
obtaining, by the reader, a series of amperometric current values wirelessly communicated from the eye-mountable device, by:
   transmitting a stabilization signal to the eye-mountable device to cause the stabilization electronics to apply the stabilization voltage between the working electrode and the reference electrode;
   transmitting a measurement signal to the eye-mountable device to cause the measurement electronics to measure an amperometric current through the working electrode and wirelessly communicate the measured amperometric current; and
   receiving, at the reader, an indication of the measured amperometric current; and
   wherein each transmission of the measurement signal immediately follows a transmission of the stabilization signal such that each of the series of amperometric current values is measured following a stabilization period during which the stabilization voltage is applied between the working electrode and the reference electrode to allow current through the working electrode caused by the stabilization voltage to reach a stable value prior to measurement.

16. The method according to claim 15, wherein the measurement signal is transmitted with a duty cycle of less than 10 percent.

17. The method according to claim 13, further comprising:
receiving, by the reader, an indication of a second measured amperometric current obtained during the measurement period; and
comparing the values of the two measured amperometric currents.

* * * * *